United States Patent
Nagao et al.

(10) Patent No.: US 12,345,648 B2
(45) Date of Patent: Jul. 1, 2025

(54) METHOD OF NON-CONTACT MATERIAL IDENTIFICATION, METHOD OF NON-CONTACT TEMPERATURE IDENTIFICATION, AND METHOD FOR IDENTIFYING PROGRESS OF HEAT TREATMENT PROCESSING

(71) Applicant: NATIONAL INSTITUTE FOR MATERIALS SCIENCE, Ibaraki (JP)

(72) Inventors: Tadaaki Nagao, Ibaraki (JP); Duc Thien Ngo, Ibaraki (JP); Ryo Tamura, Ibaraki (JP); Tung Anh Doan, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 336 days.

(21) Appl. No.: 18/026,190

(22) PCT Filed: Sep. 13, 2021

(86) PCT No.: PCT/JP2021/033443
§ 371 (c)(1),
(2) Date: Mar. 14, 2023

(87) PCT Pub. No.: WO2022/059629
PCT Pub. Date: Mar. 24, 2022

(65) Prior Publication Data
US 2023/0333023 A1    Oct. 19, 2023

(30) Foreign Application Priority Data
Sep. 16, 2020   (JP) .................. 2020-155085

(51) Int. Cl.
*G01N 21/71* (2006.01)
*G01N 21/35* (2014.01)

(52) U.S. Cl.
CPC ............ *G01N 21/71* (2013.01); *G01N 21/35* (2013.01)

(58) Field of Classification Search
CPC .............................. G01N 21/71; G01N 21/35
See application file for complete search history.

(56) References Cited

U.S. PATENT DOCUMENTS

| 4,561,786 A | 12/1985 | Anderson | |
|---|---|---|---|
| 2013/0265568 A1* | 10/2013 | Micheels | G01N 21/3577 356/51 |

FOREIGN PATENT DOCUMENTS

| JP | 2003-10989 | 1/2003 |
|---|---|---|
| JP | 2003-521687 | 7/2003 |

(Continued)

OTHER PUBLICATIONS

International Search Report issued Dec. 7, 2021 in corresponding International Application No. PCT/JP2021/033443.

(Continued)

*Primary Examiner* — David P Porta
*Assistant Examiner* — Fani Polyzos Boosalis
(74) *Attorney, Agent, or Firm* — Wenderoth, Lind & Ponack, L.L.P.

(57) ABSTRACT

Provided is to perform an identification of a temperature and/or a material of a target object to be measured in a non-contact and simple manner. A relationship between a wavelength and an emissivity of thermal radiation such as infrared rays radiated from an object is determined by the material of the object. In the present invention, the identification is performed by using this. In other words, the object above can be achieved by comparing thermal radiation intensities at a plurality of wavelengths from the given object with a database in the present invention. The database is stored by measuring the thermal radiation intensities at the plurality of wavelengths and temperatures for a plurality of (Continued)

materials in advance. An external light source is not required, and the target to be measured itself is used as a thermal radiation light source in this measurement.

20 Claims, 17 Drawing Sheets

(56) References Cited

FOREIGN PATENT DOCUMENTS

| | | |
|---|---|---|
| JP | 2019-220337 | 12/2019 |
| WO | 01/55699 | 8/2001 |

OTHER PUBLICATIONS

NDE Handbook: Non-Destructive Examination Methods for Condition Monitoring, Knud G. Boving Eds. (1987), By Elsevier Science.

T.D. Dao et al., "An On-Chip Quad-Wavelength Pyroelectric Sensor for Spectroscopic Infrared Sensing", Adv. Sci. 6, 1900579(2019).

https://spectrabase.com/, Sep. 9, 2020.

Antonio Araujo, "Multi-spectral pyrometry—a review", Meas. Sci. Technol. 28, 082002 (2017).

Jiafeng Liang et al., "Generalized inverse matrix-exterior penalty function (GIM-EPF) algorithm for data processing of multi-wavelength pyrometer (MWP)", Optics Express, vol. 26, No. 20 25706-25720 (2018).

Notice of Reasons for Refusal issued Dec. 19, 2023 in Japanese Patent Application No. 2023-550537, with English-language translation.

\* cited by examiner

M: Artificial Mica
N: Non-flammable Meta-Aramid Fiber
W: White Paint
H: Heat Resistant Inorganic Mineral Sheet

Fig. 27

Temperature (°C)

Degree of Similarity (RMSE)

| | 65 | 70 | 75 | 80 | 85 | 90 | 95 | 100 | 105 | 110 |
|---|---|---|---|---|---|---|---|---|---|---|
| | P-6 | P-5 | P-10 | P-9 | P-3 | P-10 | P-10 | P-1 | P-7 | P-9 |
| | P-10 | P-3 | P-9 | P-6 | P-6 | P-1 | P-8 | P-7 | P-9 | P-6 |
| | P-8 | P-6 | P-5 | P-8 | P-8 | P-7 | P-6 | P-10 | P-10 | P-7 |
| | P-3 | P-8 | P-2 | P-10 | P-9 | P-9 | P-9 | P-5 | P-6 | P-10 |
| | P-4 | P-9 | P-7 | P-7 | P-10 | P-4 | P-3 | P-3 | P-4 | P-4 |
| | P-9 | P-4 | P-8 | P-1 | P-4 | P-5 | P-4 | P-8 | P-3 | P-5 |
| | P-7 | P-10 | P-6 | P-5 | P-1 | P-8 | P-7 | P-9 | P-1 | P-8 |
| | P-2 | P-1 | P-3 | P-3 | P-2 | P-6 | P-1 | P-6 | P-2 | P-2 |
| | P-5 | P-2 | P-1 | P-2 | P-5 | P-3 | P-2 | P-4 | P-8 | P-3 |
| | P-1 | P-7 | P-4 | P-4 | P-7 | P-2 | P-5 | P-2 | P-5 | P-1 |
| | S-9 | S-6 | S-8 | S-9 | S-10 | S-5 | S-4 | S-2 | Z-7 | Z-1 |
| | S-10 | S-5 | S-4 | S-10 | S-9 | S-10 | S-2 | S-1 | Z-10 | Z-4 |
| | S-8 | S-7 | S-9 | S-5 | S-8 | S-7 | S-6 | S-6 | Z-5 | Z-2 |
| | S-7 | S-9 | S-5 | S-1 | S-7 | S-2 | S-1 | S-3 | Z-6 | Z-10 |
| | S-6 | S-8 | S-10 | S-8 | S-6 | S-8 | S-3 | S-4 | Z-9 | Z-9 |
| | S-5 | S-1 | S-2 | S-2 | S-5 | S-9 | S-8 | S-5 | S-3 | Z-3 |
| | S-4 | S-10 | S-6 | S-7 | S-4 | S-6 | S-9 | S-9 | Z-8 | Z-6 |
| | S-3 | S-3 | S-7 | S-3 | S-1 | S-3 | S-5 | S-7 | S-10 | Z-5 |
| | S-1 | S-2 | S-1 | S-6 | S-3 | S-1 | S-7 | S-10 | S-1 | Z-7 |
| | S-2 | S-4 | S-3 | S-4 | S-2 | S-4 | S-10 | S-8 | Z-1 | Z-8 |
| | 65 | 70 | 75 | 80 | 85 | 90 | 95 | 100 | 105 | 110 |

P: Polyimide Sheet
S: Silicone Rubber Sheet
Z: Porous Zirconia

METHOD OF NON-CONTACT MATERIAL IDENTIFICATION, METHOD OF NON-CONTACT TEMPERATURE IDENTIFICATION, AND METHOD FOR IDENTIFYING PROGRESS OF HEAT TREATMENT PROCESSING

TECHNICAL FIELD

The present invention relates to a method for identifying a material and a state of a target to be measured and/or a temperature thereof in a non-contact manner, and more particularly to a method for performing the identification by using thermal radiation from the target to be measured. The present invention also relates to a method for identifying the progress of a processing by heat treatment or for identifying modification or deterioration of the material.

BACKGROUND ART

As is well known, any object radiates fixed electromagnetic waves (infrared rays in a normal temperature range) based on a temperature thereof. Devices called pyrometer, thermography, and the like, in which this phenomenon (called the thermal radiation or heat radiation) is utilized to measure infrared rays radiated from the object and obtain a surface temperature of the object, have been provided (for example, pages 310 to 320 of Non Patent Literature 1). However, since an emissivity of infrared radiation from the object varies depending on not only the temperature but also the material of the surface and the like, the surface temperature cannot be accurately obtained only by simply measuring an amount of the infrared rays radiated. Therefore, in a case of an object with a known emissivity, it is possible to obtain the surface temperature with high accuracy by using the pyrometer or the thermography through calibrating a temperature dependence of the amount of infrared rays and the emissivity for the material of a surface of the object. With this accuracy, a magnitude correlation of a relative temperature of the same material or the object can be identified in increments (resolution) of about 0.05 K in a case of the thermography with high accuracy, but an absolute value accuracy of the obtained temperature is about 1 to 2%. The latter accuracy is an error caused by an emissivity value accuracy provided in advance for each material, sensitivity of a photodetector device, an environmental temperature, and the like. In a case where information on the kinds of materials of the object surface and the emissivity is not separately provided, the absolute value accuracy of the temperature is not guaranteed, and a large error occurs.

As an approach for the case where information on the kinds of materials of the object surface and the emissivity is not separately provided, a method (a two-color method) has been proposed, in which it is assumed that, wavelength dependence of the emissivity is small (is or can be considered as a constant), and an influence of an error due to the emissivity is reduced by measuring and calculating the infrared light for two wavelengths (Patent Literature 1).

Here, an example will be explained with reference to FIG. 1 and FIG. 2 in which an epoxy is used as a target object to be measured, and radiation temperature measurement is performed via the two-color method by using two sensors with high wavelength resolution in a wavelength range where the emissivity can be considered as the constant.

FIG. 1 shows an emissivity function of the epoxy and a change in spectral radiation intensity of a black body and an epoxy sample depending on the wavelength. An emissivity $\varepsilon$ of the epoxy can be considered as almost the constant between two wavelengths at a very narrow interval (for example, the wavelength region of 3.5 µm to 4 µm) ($\varepsilon$=0.88 to 0.92). FIG. 1 further shows sensitivity curves of dual-band infrared sensors with high wavelength resolution, which have peaks at two wavelengths $\lambda_1$ and $\lambda_2$ within the wavelength range of 3.5 µm to 4 µm, and can perform detection with high wavelength resolution for two adjacent wavelengths within such narrow wavelength region. As an example of producing such infrared sensor, for example, please refer to Non Patent Literature 2.

Here, for each wavelength $\lambda_1$, $\lambda_2$, thermal radiation intensities $L(\lambda_1,T)$, $L(\lambda_2, T)$ (hereinafter, these may be abbreviated as $L_1$ and $L_2$, respectively) at a temperature T, $\varepsilon(\lambda)$ as the emissivity and $B(\lambda,T)$ as the Planck's radiation formula:

$$L(\lambda_1, T) = \varepsilon(\lambda_1) B(\lambda_1, T)$$

$$L(\lambda_2, T) = \varepsilon(\lambda_2) B(\lambda_2, T)$$

can be placed. By dividing the formulas above by sides, $$L_1/L_2 = L(\lambda_1, T)/L(\lambda_2, T)$$
$$= [\varepsilon(\lambda_1)/\varepsilon(\lambda_2)] \cdot [B(\lambda_1, T)/B(\lambda_2, T)]$$

is obtained. Here, when the emissivity value is substantially constant at two adjacent wavelengths $\lambda_1$ and $\lambda_2$, that is, when $\varepsilon(\lambda_1)/\varepsilon(\lambda_2) \approx 1$, an emissivity $\varepsilon(\lambda)$ is eliminated from the formula above, and $$L_1/L_2 \approx B(\lambda_1, T)/B(\lambda_2, T)$$

can be placed. Here, since the thermal radiation intensities $L_1$ and $L_2$ at the wavelengths $\lambda_1$ and $\lambda_2$ can be measured, and functions of the Planck's radiation formula on a right side of the formula above are known, the temperature T of a sample of the target to be measured (the epoxy in the example shown in FIG. 1) can be obtained from a ratio value of respective thermal radiation intensities $L_1$ and $L_2$ measured at the adjacent wavelengths $\lambda_1$ and $\lambda_2$.

An example of actual temperature measurement by performing infrared measurement at two wavelengths $\lambda_1$ and $\lambda_2$ (here, $\Delta\lambda \equiv \lambda_2 - \lambda_1$) in the wavelength region in which the emissivity $\varepsilon$ can be considered to be substantially constant within a certain wavelength range by using the two-color method generally explained above is shown below. Here, the epoxy described above was used as the material of the target to be measured, and for the wavelengths at which the measurement was performed, the wavelength $\lambda_1$ on a short wavelength side was fixed at 3.5 µm, and the wavelength $\lambda_2$ on a long wavelength side was 3.6 µm, 3.7 µm, 3.8 µm, and 3.9 µm ($\Delta\lambda$ is 0.1 µm, 0.2 µm, 0.3 µm and 0.4 µm, respectively). Further, a sensor having a wavelength resolution of 0.05 µm was used as the wavelength-selective infrared sensor.

In FIG. 2, a solid curve is a graph obtained by determining and plotting the ratio value ($L_2/L_1$) of the thermal radiation $L_1$ and $L_2$ at the wavelengths $\lambda_1$ and $\lambda_2$, that is, an energy ratio between the thermal radiation at these two wavelengths when a temperature of a perfect black body is changed in a range from around a room temperature to 700 K. It is noted that a plot range of the temperature was set to 300 to 700 K. On the other hand, an energy ratio is obtained from the thermal radiation from the epoxy at the same wavelengths $\lambda_1$ and $\lambda_2$ in the same manner as in a case of the perfect black body, and is shown as a broken line curve in FIG. 2. As described above, since the wavelengths $\lambda_1$ and $\lambda_2$ are within a range where the emissivity of the epoxy can be considered as substantially constant, the energy ratio thereof should be on the substantially same curve as the energy ratio in the case of the perfect black body. A temperature of the epoxy was estimated from a calculation result shown in FIG. 2 by using this. On the other hand, the temperature of the epoxy was accurately determined via another measurement method, and a difference between the estimated temperature and the accurately determined temperature of the epoxy was obtained. This difference was taken as an error in the temperature measurement between the perfect black body and the epoxy which is the material of the target to be measured. Results thereof are shown in a table below.

TABLE 1

| $\lambda_1/\lambda_2$ (μm) | $\Delta\lambda$ (μm) | Difference of temperature measurement between perfect black body and epoxy |
|---|---|---|
| 3.5/3.6 | 0.1 | 5.6 |
| 3.5/3.7 | 0.2 | 3.2 |
| 3.5/3.8 | 0.3 | 2.3 |
| 3.5/3.9 | 0.4 | 5.1 |

As can be seen from the table, the temperature of the target to be measured can be measured with an error of about 2 to 6 K under the conditions above. Further, in this experiment by using a sensor with the wavelength resolution of 0.05 μm, the highest accuracy can be obtained when $\Delta\lambda=0.3$ μm or so. As the wavelength interval $\Delta\lambda$ is further narrowed, a difference in the emissivities between the two wavelengths at which the thermal radiation is measured is reduced, and thus it seems to be considered that measurement accuracy is improved, but it is found that a temperature estimation result is sensitive to a small variation in the emissivity, and thus on the contrary, the accuracy is determined as degraded.

As described above, when the emissivity can be considered as substantially constant in the certain wavelength range, the temperature of the target to be measured can be estimated with high accuracy by using the two-color method. On the contrary, however, it has been difficult to reduce an error of the surface temperature obtained by using the pyrometer or the thermography in a case where information on the material and the property of the object surface is not provided at all or in a case where the wavelength dependence of the emissivity of the object surface is large and cannot be considered as the constant. Further, similarly to thermography, it has not been easy to identify various materials constituting the object in a non-contact measurement environment.

In a field of analytical chemistry, it is known to identify the material by using an infrared absorption spectrum of FTIR. For example, as shown in Non Patent Literature 3, a database exists, in which a spectrum thereof is presented when a molecule is selected and then Raman, ATR-IR, transmitted IR, or the like is selected. It is possible to identify a certain degree of materials by checking whether a measured infrared absorption spectrum is similar to that from the material at which it is aimed by using such database. However, in such method for identifying the material from the infrared absorption spectrum, a case exists where the material of the object made of a single material can be identified, but identification of the object made of a mixture is not easy. Further, in a case where optimization of baseline correction is performed or a material having a complicated spectrum due to overlapping of a large number of absorption bands is discriminated, human judgment needs to be kind of interposed. Further, this method requires a powerful infrared light source and a Michelson interferometer, and is not suitable for IR remote sensing using an on-chip small sensor. In addition to this, the spectrum as described in Non Patent Literature 3 has a sharp peak due to molecular vibration. In such case, it is relatively easy to identify the material based on the number of peaks, values of the wavelengths, ratios of the intensities, and the like, but it is usually difficult to identify the material based on a spectrum not having such sharp peak.

Non Patent Literature 4 has a review on latest trends of infrared radiation temperature measurement. From a conclusion of this review and more, it is found that various restrictions such as specific conditions and kinds of materials are necessary for a method of a multi-wavelength analysis assuming the emissivity function. It is considered that a current state of this technology is that many restrictions and problems still exist just in the determination of the temperature, and that research has not progressed to a stage of material identification.

Further, the research exists in which the temperature is measured by using the thermal radiation as described above in fields of applied physics and mechanical engineering fields. In these studies, a method of obtaining the temperature after obtaining an emissivity function $\varepsilon(\lambda)$ is also proposed in order to increase radiation temperature measurement accuracy. Hereinafter, this method for temperature estimation is referred to as a multi-wavelength analysis method. However, identifying a material by using a fact that the emissivity function $\varepsilon(\lambda)$ is obtained has not been proposed. A reason thereof is that as a problem before such an application is performed, a problem exists in which a solution cannot be uniquely obtained because an unknown number is N+1 (specifically, a value of the emissivity $\varepsilon_n$ at the N wavelengths $\lambda$+the temperature T, wherein $1 \leq n \leq N$) when the infrared measurement is performed at N wavelengths $\lambda$. In addition, in obtaining the emissivity function $\varepsilon(\lambda)$, when initial values of the emissivity $\varepsilon_n$ and the temperature T at each wavelength $\lambda$ are close to true values, a highly accurate solution can be obtained, but when these initial conditions are far from the true values, the accurate solution cannot be obtained. This problem in the multi-wavelength analysis method will be specifically explained below with examples.

FIG. 3 shows results of estimating the emissivities by performing least squares fitting through using anodized alumina as the material of the target to be measured, and by assuming a sine function and a cubic function as function forms of the emissivities. In FIG. 3, the solid curves in graphs of the emissivities indicate true emissivities, and circle marks in the graphs of the emissivities on an upper side and a lower side indicate initial values and results of the least squares fitting, respectively. Further, in graphs of the radiation intensities, the circle marks in each of two upper and lower graphs indicate measured values of the radiation intensities, and broken lines in the graphs of the radiation intensities on the lower side indicate the least squares fitting results, that is, the results of adjusting the emissivity functions so that curves of the radiation intensities well fit the measured values of the radiation intensities. Furthermore, the broken lines in the graphs of the radiation intensities on the upper side are curves obtained by appropriately setting initial values of the temperature and multiplying the Planck's radiation formula of the temperature by the initial values of the emissivities indicated by the circle marks. In this curve, a deviation increases when an initial temperature is low.

FIG. 3 also shows the fitting results when a specific functional form is not assumed for the emissivity functions. It appears that a suitable fitting has been performed in FIG. 3. However, in a case where the emissivities are complicated functions, the fitting itself is possible, but it is required to artificially induce the initial values at that time, that is, to set the initial values in anticipation of appropriate fitting results of what true emissivity functions approximately are. Without such artificial induction of the initial values, the values do not converge to a reasonable solution in most cases. In a case where a function of a spectral emissivity is complicated, the fitting is simpler when the functional form is not set as shown at a right end of FIG. 3, but the artificial induction of the initial values is still necessary. In addition, in a case where the functional form of the emissivities is specified in the fitting, a flexibility of the fitting is limited depending on a selected functional form, and sometimes the fitting cannot be well performed. On the other hand, when the function is not determined and the emissivity values of each point are independently determined for each wavelength by using the emissivity values of each point as a fitting variable, a limitation of the functional form is eliminated, and even when the emissivities change steeply and violently, the fitting can be always performed. As a result, the fitting can be performed with higher accuracy.

The artificial induction of the initial values during the fitting described above will be explained with reference to examples shown in FIG. 4. FIG. 4 uses the same material of the target to be measured and data of radiation intensity measurement as in FIG. 3, and shows fitting results for three cases where the initial value of an estimated temperature T' is 300 K in the fitting, and the initial values of the emissivity function $\varepsilon(\lambda)$ are 0.2, 0.5, and 0.8, which are constant values at 0.2 μm increments between 3.0 μm and 4.0 μm in wavelength, and the estimated temperature obtained by the fitting results. In addition, the actual temperature T of the target to be measured was 350 K. As can be seen from the graphs, the smaller the deviation between the initial values (the circle marks) of the emissivities shown in the upper graphs and the actual emissivities (the solid curves), that is, the more to the right of the three cases, the smaller the deviation between the emissivities of the least squares fitting result (the circle marks in the graphs of the emissivities on the lower side) and the actual emissivities (the solid curves in the graphs) is, and as a result, the smaller a deviation $\Delta T$ value from the actual temperature T of the estimated temperature T' after the least squares fitting estimated therefrom is. From these results, it can be seen that a fitting result with high accuracy is obtained as the initial values are closer to a correct solution, that is, the fitting with high accuracy cannot be realized unless information on the target to be measured is kind of known in advance.

Since conventional organic and inorganic materials (bulk materials) around us have a large thickness, the emissivity tends to increase in an entire wavelength region (however, a specular metal has a small emissivity $\varepsilon$ and does not correspond thereto). Accordingly, increasing the initial values of the emissivity function $\varepsilon(\lambda)$ (for example, about 0.9) often increases the temperature measurement accuracy in a case where multi-wavelength fitting of the emissivity function described above is performed. FIG. 5 shows tiles, bricks, and concrete that are conventional building materials as examples of such materials and these materials have the emissivity $\varepsilon$ in a range of approximately 0.8 to 1. FIG. 5 also shows that temperature estimation with high accuracy can be realized by performing the fitting with the initial value of the emissivity function $\varepsilon(\lambda)$ in a wavelength range of 3 to 4 μm set to 0.9. FIG. 5 also lists examples of glass. As shown here, since the value of the emissivity function $\varepsilon(\lambda)$ of glass is about 0.6 in the wavelength region of 3 to 4 μm, it is possible to perform the temperature estimation with high accuracy by setting the initial value to 0.6.

As described above, the multi-wavelength fitting of the emissivity function $\varepsilon(\lambda)$ enables the temperature estimation with high accuracy, however, at that time, it is required to kind of obtain information on the emissivity of the target to be measured in advance. Accordingly, in a case where an approximate value of the emissivity of the material of the target to be measured is not known in advance, in a case where the approximate value of the emissivity is not provided when the material is known, or the like, this method is mostly not applicable.

Non Patent Literature 5, in which it is stated that the problem above in obtaining the emissivity function is solved, has been published. In Non Patent Literature 5, it is described that an accurate temperature can be obtained regardless of the initial conditions (that is, in a case where the emissivity function of the material is not known). Specifically, the radiation intensities from the target object to be measured at a plurality of wavelengths are measured, and the temperature of the object is obtained by a newly proposed Generalized Inverse Matrix-Exterior Penalty Function (GIM-EPF) data processing algorithm. However, although it is disclosed that a GIM-EPF algorithm requires less computation time than conventional algorithms, it is still complexed and requires considerable computational power for data processing. Further, in a specific example shown in Non Patent Literature 5, only six kinds of materials is used, and there is no verification of whether or not the algorithm can function equally for various materials. Further, the application temperature is only in a visible-near infrared band at which visible light is emitted at 1600 K or more, and there is no verification of whether or not the algorithm equally functions at a temperature equal to or lower than the visible-near infrared band. Furthermore, there is no suggestion that the GIM-EPF algorithm is used to discriminate the material. If such discrimination is attempted within a scope described in Non Patent Literature 5, whether or not it is possible is uncertain.

SUMMARY OF INVENTION

Technical Problem

Accordingly, it is an object of the present invention to easily identify a material or a state constituting a target object to be measured in a non-contact manner by measuring electromagnetic waves such as infrared rays radiated from the target to be measured. Furthermore, it is also an object of the present invention to determine a surface temperature of the target to be measured on essentially the same principle as material identification.

Solution to Problem

According to one aspect of the present invention, provided is a method for identifying a material in a non-contact manner by measuring a target to be measured as a thermal radiation light source, which includes: comparing degrees of similarity between intensity data and at least one of reference data and combined reference data, the intensity data being a combination of thermal radiation intensities at three wavelengths or more wavelengths in an infrared band radiated from the target to be measured itself, the reference data being a combination of thermal radiation intensity data at a plurality of wavelengths in the infrared band from each of a plurality of different candidate materials for identifying a material of the target to be measured, and the combined reference data being of a mixture of the plurality of different materials obtained by combining a plurality of pieces of the reference data based on the plurality of different materials; and identifying the material of the target to be measured as the candidate material or a mixture thereof corresponding to one or more pieces of the reference data or the combined reference data having the highest degree of similarity.

The comparison of the degrees of similarity may be performed at least for all pieces of the combined reference data.

Further, a solving method for the combinatorial optimization problem may be applied to the comparison of the degrees of similarity and the identification.

Further, processing may be performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

Further, the target to be measured may be a solid, a liquid, a gas, or a mixture thereof.

Further, the reference data may be intensity data measured at a plurality of discrete wavelengths.

Further, the plurality of wavelengths may be at least three wavelengths.

Further, the degrees of similarity may be determined based on a difference in intensities between the intensity data and the reference data at the plurality of wavelengths.

Further, the reference data may be a combination of a plurality of temperatures that are candidates for material identification of the target to be measured and the thermal radiation intensity data at the plurality of wavelengths in the infrared band for each of the plurality of different materials.

Further, the degrees of similarity may be determined based on a difference in intensities between the intensity data and the reference data at the plurality of wavelengths for each temperature.

Further, the degrees of similarity may be obtained after normalizing each piece of the intensity data and the reference data.

Further, thermal radiation from an object other than the target to be measured may be removed using an optical system.

Further, the optical system may be a curved mirror such as a parabolic mirror, a flat mirror, a lens or an iris using an infrared transmitting material, or a combination thereof.

Further, the degrees of similarity may be determined based on a root mean square error between the intensity data and the reference data.

According to another aspect of the present invention, provided is the method for identifying at least one of a material and a temperature in a non-contact manner by measuring a target to be measured as a thermal radiation light source, which includes: comparing degrees of similarity between intensity data and at least one of reference data and combined reference data, the intensity data being a combination of thermal radiation intensities at three wavelengths or more wavelengths in an infrared band radiated from the target to be measured itself, the reference data being is a combination of thermal radiation intensity data at a plurality of wavelengths in the infrared band for each of a plurality of known temperatures from each of a plurality of different candidate materials for identifying a material of the target to be measured, and the combined reference data being of a mixture of the plurality of different materials obtained by combining a plurality of pieces of the reference data based on the plurality of different materials; and identifying the material and/or the temperature of the target to be measured as a material or a mixture thereof, and/or a temperature corresponding to one or more pieces of the reference data or the combined reference data having the highest degree of similarity.

The comparison of the degrees of similarity may be performed at least for all pieces of the combined reference data.

Further, a solving method for the combinatorial optimization problem may be applied to the comparison of the degrees of similarity and the identification.

Further, processing may be performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

Further, the target to be measured may be a solid, a liquid, a gas, or a mixture thereof.

Further, the reference data may be intensity data measured at a plurality of discrete wavelengths.

Further, the plurality of wavelengths may be at least three wavelengths.

Further, the degrees of similarity may be determined based on a difference in intensities between the intensity data and the reference data at the plurality of wavelengths for each temperature.

Further, the degrees of similarity may be obtained after normalizing each piece of the intensity data and the reference data.

Further, thermal radiation from an object other than the target to be measured may be removed using an optical system.

Further, the optical system may be the curved mirror, the flat mirror, the lens or the iris using the infrared transmitting material, or the combination thereof.

Further, the degrees of similarity may be determined based on a root mean square error between the intensity data and the reference data.

According to still another aspect of the present invention, provided is a method for identifying a product during processing, or a state of the processing, a progress of the processing, or normality of the processing in a heat treatment process, which includes: comparing degrees of similarity between intensity data and at least one of reference data and combined reference data for each predetermined step of processing in a heat treatment process of a material, the intensity data being a combination of thermal radiation intensities at a plurality of wavelengths in an infrared band radiated from the material itself, the reference data being a combination of the thermal radiation intensities at the plurality of wavelengths in the infrared band radiated from the same kind of the material itself obtained at predetermined steps of processing in a heat treatment process of a plurality of different materials of the same kind as the material, and the combined reference data being of a mixture of the plurality of different materials obtained by combining the plurality of pieces of the reference data based on the plurality of different materials; and identifying one or more pieces of the reference data or the combined reference data having the highest degree of similarity.

The comparison of the degrees of similarity may be performed at least for all pieces of the combined reference data.

Further, a solving method for the combinatorial optimization problem may be applied to the comparison of the degrees of similarity and the identification.

Further, processing may be performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

Further, the plurality of wavelengths may be at least three wavelengths.

Further, the reference data may further include a combination of the thermal radiation intensities at the plurality of wavelengths in an infrared band radiated from a defective material itself that can be generated by abnormal progress in the heat treatment process of the material.

Further, the degrees of similarity may be obtained after normalizing each piece of the intensity data and the reference data.

Further, the degrees of similarity may be determined based on a difference in intensities between the intensity data and the reference data at the plurality of wavelengths.

Further, the degrees of similarity may be determined based on a root mean square error between the intensity data and the reference data.

According to still another aspect of the present invention, provided is a method for detecting a material change that is a change of a material being a target to be measured from a reference material, by comparing degrees of similarity between intensity data and at least one of reference data and combined reference data, the intensity data being a combination of thermal radiation intensities at a plurality of wavelengths in an infrared band radiated from the material of the target to be measured itself, the reference data being a combination of the thermal radiation intensities at the plurality of wavelengths in the infrared band radiated from the reference material itself that is a plurality of different materials of the same kind as the material of the target to be measured, and the combined reference data being of a mixture of the plurality of different materials obtained by combining the plurality pieces of reference data based on the plurality of different materials, and identifying one or more pieces of the reference data or the combined reference data having the highest degree of similarity.

The comparison of the degrees of similarity may be performed at least for all pieces of the combined reference data.

Further, a solving method for the combinatorial optimization problem may be applied to the comparison of the degrees of similarity and the identification.

Further, processing may be performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

Further, the reference data may be intensity data measured at a plurality of discrete wavelengths at a plurality of temperatures.

Further, the degrees of similarity may be obtained after normalizing each piece of the intensity data and the reference data corresponding to the target to be measured.

Further, the degrees of similarity may be determined based on a difference in intensities between the intensity data corresponding to the target to be measured at the plurality of wavelengths and the reference data.

Further, thermal radiation from an object other than the target to be measured may be removed using the optical system.

Further, the optical system may be a curved mirror, a flat mirror, a lens or an iris using an infrared transmitting material, or a combination thereof.

Further, the degrees of similarity may be determined based on a root mean square error between the intensity data corresponding to the target to be measured and the reference data.

Further, the change may be a change over time.

Further, the reference data may further include the intensity data upon the reference material changing to an abnormal state.

Further, the material of the target to be measured may be the same individual as the reference material.

Further, the material of the target to be measured may be an individual different from the reference material.

Advantageous Effects of Invention

According to the present invention, intensities of the electromagnetic waves such as the infrared rays radiated from the target object to be measured are measured at one or the plurality of temperatures or the plurality of wavelengths, and the measured intensities are compared with a set of temperature-wavelength-intensity of a plurality of candidate materials separately measured, whereby the material constituting the target object to be measured can be easily identified in the non-contact manner without irradiating the target object to be measured with the infrared rays or the like. In the present invention, by measuring a set of data of wavelength-radiation intensities from the candidate materials at the plurality of temperatures, material identification accuracy can be dramatically increased, and the surface temperature of the target object to be measured can also be obtained at the same time. In addition, when the temperature of the target to be measured is known, it is also possible to specify the material only by comparing the candidate materials with a pair of wavelength-intensity at the known temperature. In a spectrum of the thermal radiation, a component changing slowly according to the Planck radiation is large as compared with a fine spectrum caused by the molecular vibration, and a fine peak is mostly not sharp. According to the present invention, it is possible to easily and accurately identify the material and the temperature of the target to be measured regardless of such characteristics of the thermal radiation.

BRIEF DESCRIPTION OF DRAWINGS

FIG. 27 shows the material discrimination result in the case where measurement is repeated in one example of the present invention, where a polyimide thin film is the unknown sample. They are arranged in the descending order of degrees of similarity. The polyimide ranked high, and the unknown material was determined to be polyimide with high accuracy.

DESCRIPTION OF EMBODIMENTS

Figure 1:
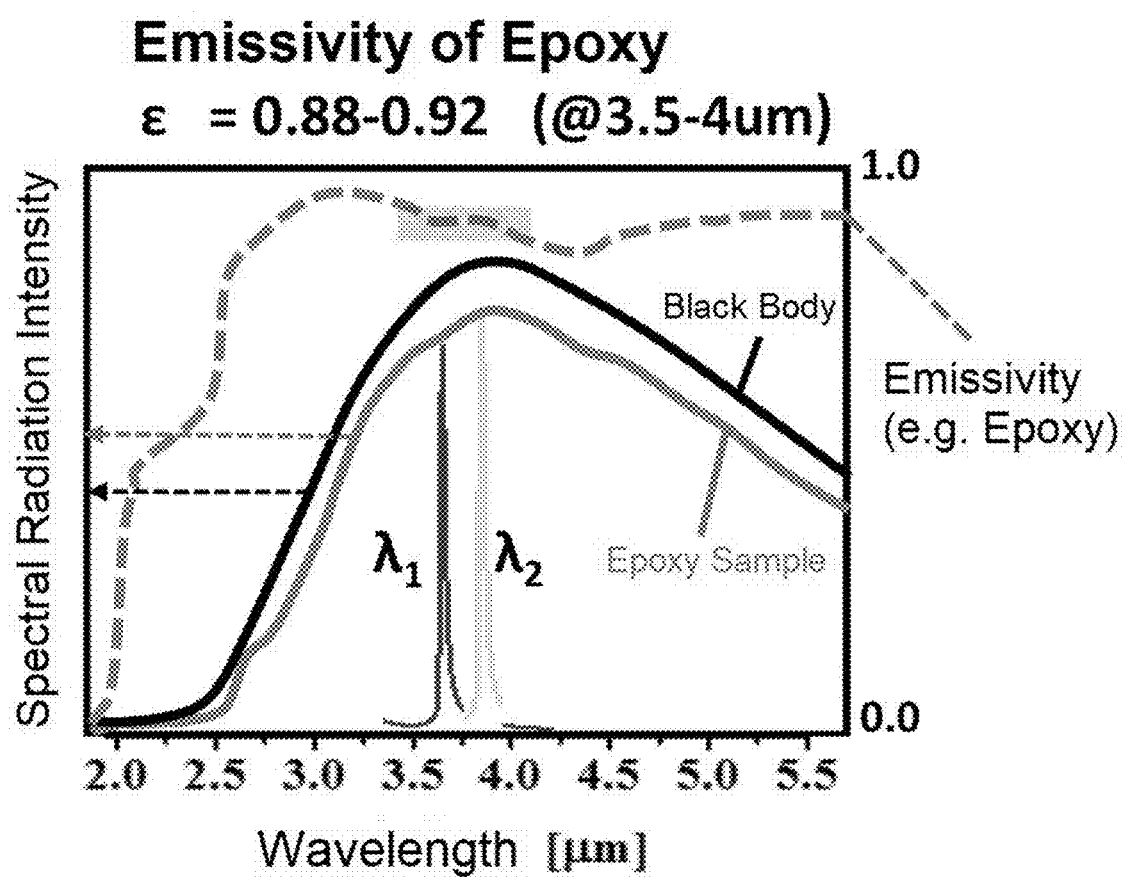
FIG. 1 is a diagram for explaining radiation temperature measurements by two-color method according to the prior art.
Figure 2:
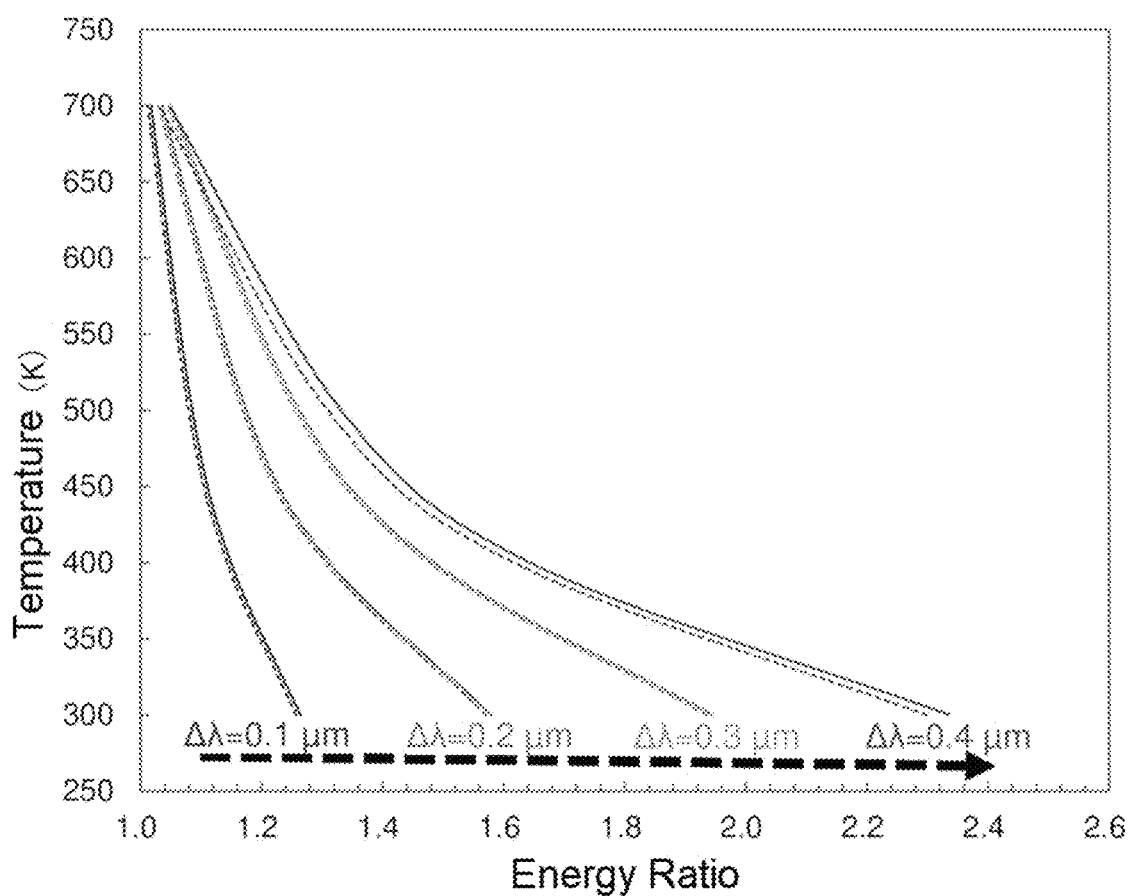
FIG. 2 shows graphs obtained by calculating and plotting ratio values ($L_2/L_1$) of thermal radiation $L_1$ and $L_2$ at the wavelengths $\lambda_1$ and $\lambda_2$, that is, the energy ratio between the thermal radiation at these two wavelengths when temperatures of a perfect black body and an epoxy are changed in the range from around the room temperature to 700 K.
Figure 3:
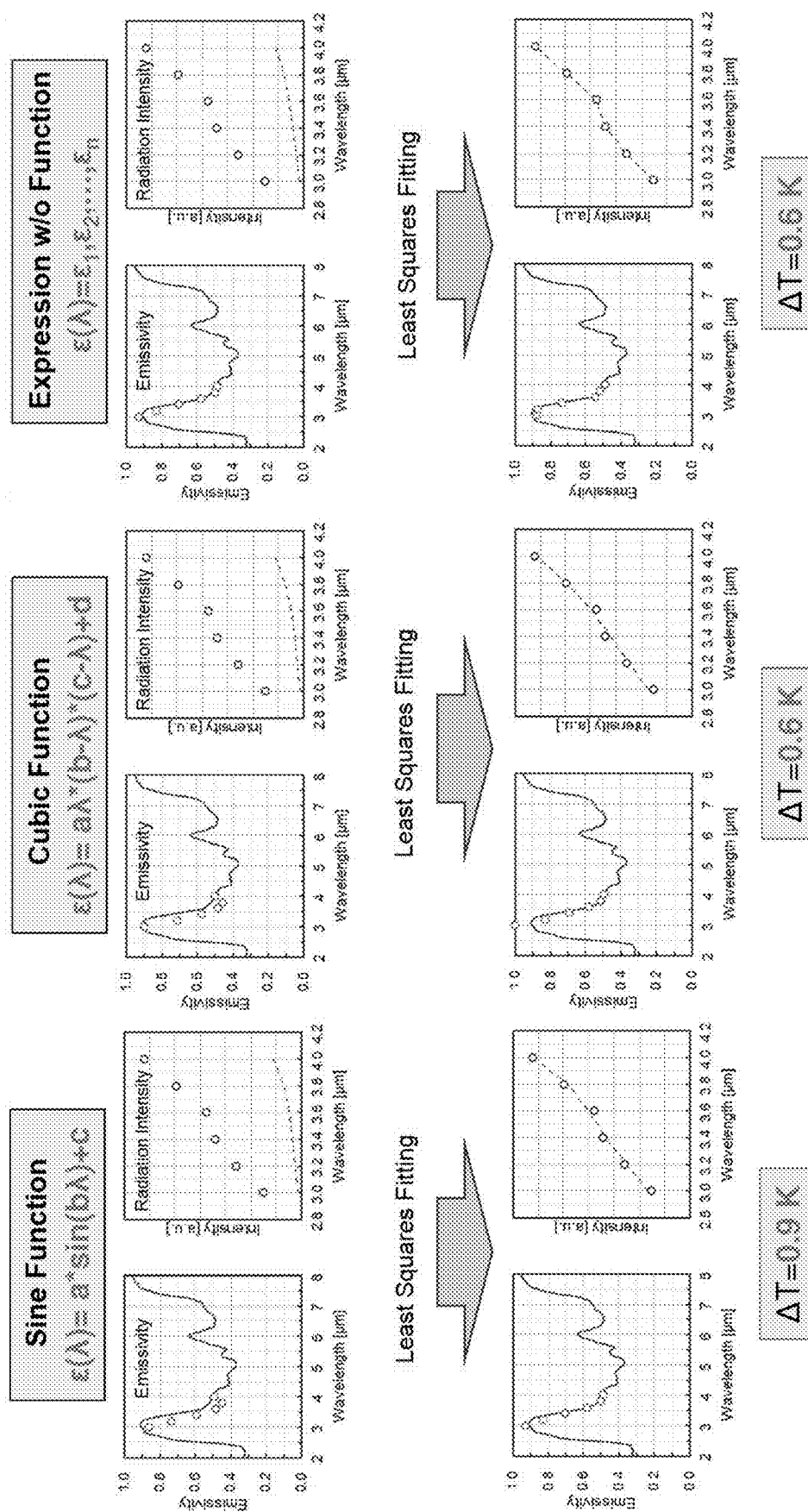
FIG. 3 provides an explanation of a temperature estimation method by using multi-wavelength analysis according to the prior art. An example of a problem that it is necessary to know the information on the emissivity of a material of a target object to be measured in advance in order to perform the temperature estimation with high accuracy is shown.
Figure 4:
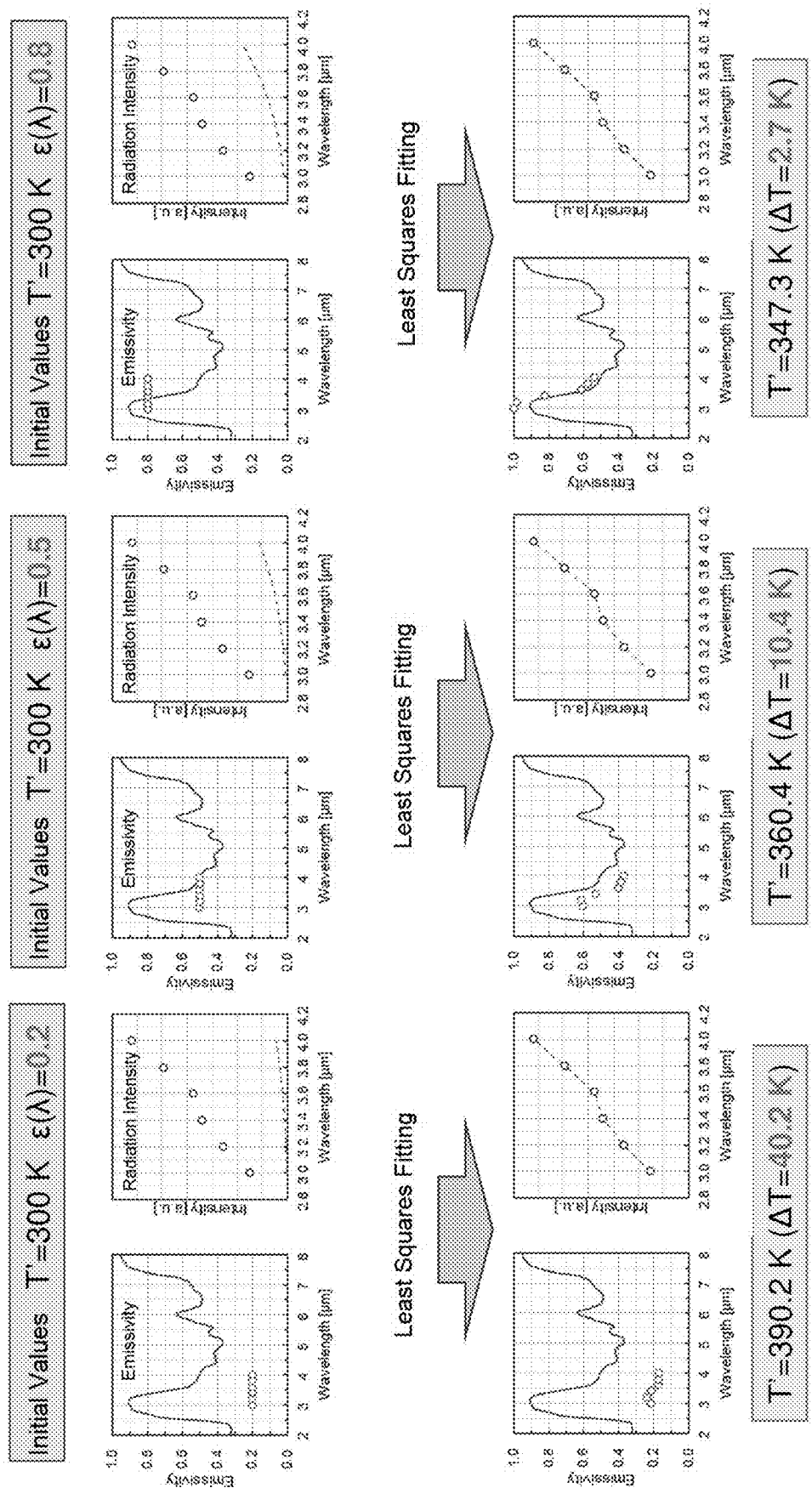
FIG. 4 more specifically presents the problem shown with reference to FIG. 3.
Figure 5:
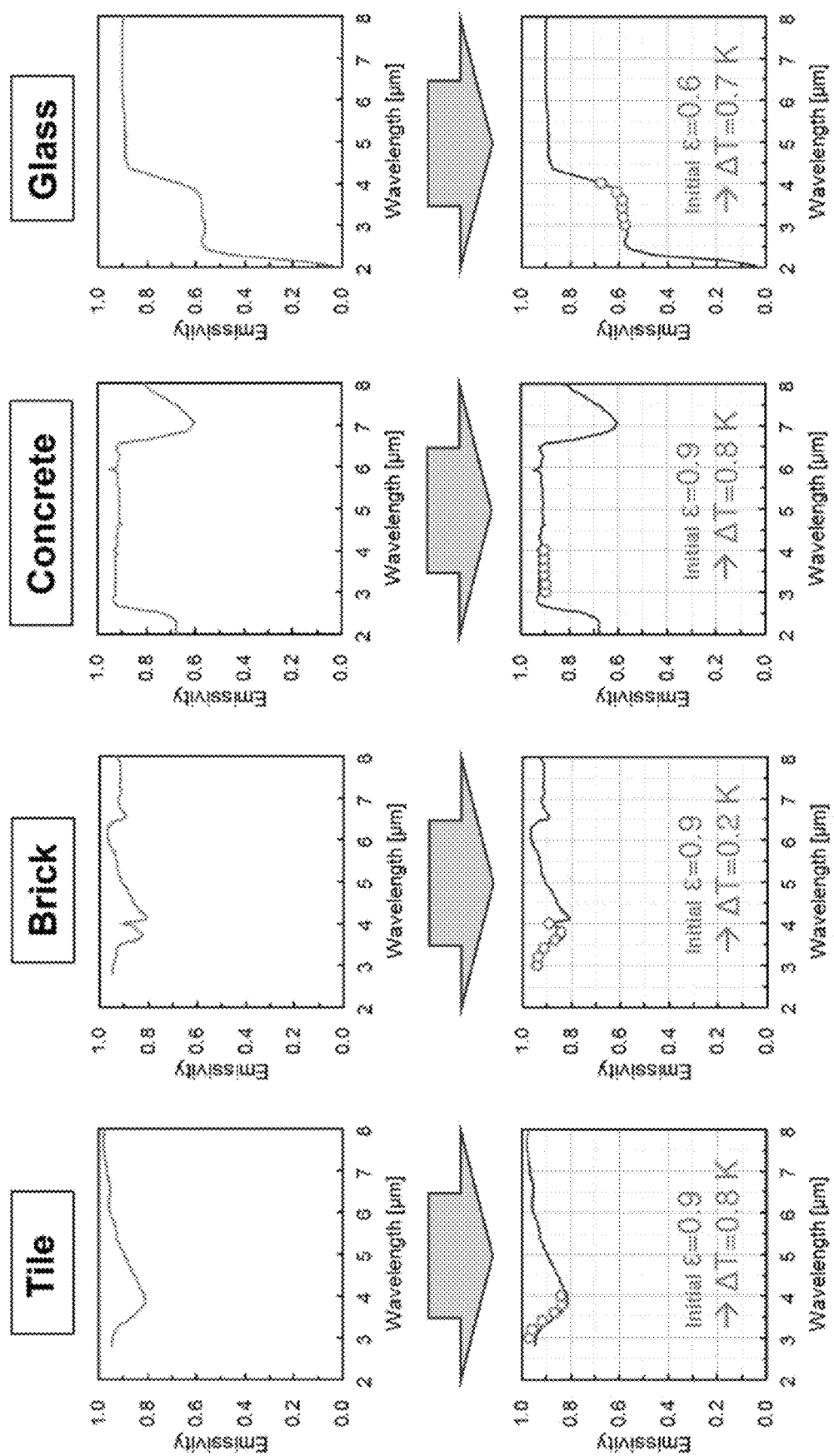
FIG. 5 more specifically presents the problem shown with reference to FIG. 3.

According to one embodiment of the present invention, a wavelength-temperature-intensity combination of the electromagnetic waves such as the infrared rays (typically, a mid-infrared region (wavelength: 2.5 to 30 μm)) radiated from a target object to be measured itself is measured to identify the material constituting the object and the temperature of the object. Here, the wavelength-temperature-intensity combination above can be generally expressed as a continuous function $I=f_T(\lambda)$ in which the temperature T from the wavelength λ to a thermal radiation intensity I on a continuous wavelength range is used as a parameter. However, it is usually more practical to preferably consider the discrete wavelengths. In this case, the wavelength-temperature-intensity combination above is a set of triplets ($\lambda_m$, $T_n$, $I_p$) of measurement values of the thermal radiation intensities $I_1, \ldots,$ and $I_P$ at discrete wavelengths $\lambda_1, \ldots,$ and $\lambda_m$ and discrete temperatures $T_1, \ldots,$ and $T_N$ (here, m, n, and p are integer values in the ranges of $1 \leq m \leq M$, $1 \leq n \leq N$, and $1 \leq p \leq P$, respectively). In the present application, the above continuous function and the set of triplets of the measurement values are collectively referred to as reference data (individual reference data) for measurement results of a candidate material to be identified, and referred to as data of a target to be measured for measurement results of the target to be measured. The discrete wavelengths are at least three wavelengths, and more preferably four or more wavelengths. In addition, in a mid-infrared wavelength range, 3 to 4.2 μm and 8 to 14 μm, which are called atmospheric air windows, can be used for remote sensing at a distance of about several meters or more. A vicinity of 2.5 to 4.5 μm is advantageous when a high-temperature object such as ceramic or metal is measured because a rising edge of the Planck radiation is steep. Further, a wavelength range of 14 μm or more is effective for measuring a low-temperature object. Accordingly, it is advantageous to properly use the wavelength range for measuring the reference data and the data of the target to be measured according to the application. For example, 2.5 to 4.5 μm may be used in a case where the temperature of a target object at a relatively short distance is high at a manufacturing site such as a factory; 4.5 to 14 μm may be used in an application where an object for daily use of which temperature is near the room temperature is recognized, an IoT device application, or the like; and 14 to 30 μm may be used in a case where the temperature of a target is low in an application such as drug discovery and medical use. In order to perform the identification, a combination is measured and accumulated in a database as the reference data. The combination is made of the radiation intensities of the electromagnetic waves radiated from a plurality of kinds of candidate materials (hereinafter, also referred to as the reference material) at the plurality of temperatures and at the plurality of wavelengths (multi-temperature and multi-wavelength intensity data). The combination (the data of the target to be measured) of the electromagnetic wave intensities radiated from the target object to be measured is compared with the reference data accumulated in the database, and one piece of reference data having the highest degree of similarity or the plurality of pieces of reference data having high degrees of similarity is obtained. Since the material and the temperature thereof are associated with each piece of reference data accumulated in the database, it is possible to identify one material having the highest degree of similarity with the material of the target to be measured or identify a plurality of kinds of material candidates having high degrees of similarity. Further, the temperature of the target to be measured can also be identified at this time. It is natural that, both the material and the temperature of the target to be measured may be identified and results thereof may be presented, or only one thereof may be presented. Here, as a point that should be noted, the present invention does not measure light appearing as a response to irradiation with an incident light from the light source, such as conventional FTIR and Raman spectra. In the invention of the present application, the electromagnetic waves radiated by using the target object to be measured itself as a light source, that is, the electromagnetic waves that are determined by the temperature of the target object to be measured and are not directly related to a presence or absence of the incident light, are measured.

In order to set the temperature of the target object to be measured, it is necessary to heat and/or cool the object, but a means therefor is not particularly limited. Specific examples include heat conduction through a stage on which the object is placed, heat conduction from an atmosphere around the object, such as blowing hot air or cold air. When only heating is required, microwave heating, heating by the thermal radiation from a heat source, and the like can be used. In addition, when the reference data is being sought while heating or cooling is performed, a means for measuring the surface temperature of the target to be measured as accurately as possible is required. However, although there is a difference in degrees depending on the means of heating/cooling, for example, when the temperature measurement is performed by a thermocouple or the like provided inside or on a back surface of the object, the temperatures inside or on the back surface may not be necessarily the same as a temperature of a front surface. When such difference in temperatures depending on a place becomes a problem, for example, it is possible to take measures such as minimizing an error by making a temperature of an entire object as uniform as possible by continuing heating for a sufficiently long time under certain conditions. Further, in a situation where the temperature on a front side of the target object to be measured is measured, the temperature may differ depending on places. When such difference in the temperatures depending on the places becomes the problem, for example, by using the curved mirror such as the parabolic mirror, the flat mirror, the lens using the infrared transmitting material (for example, silicon oxide, Si, and Ge), the iris, or an infrared optical system in which these mirrors are combined, it is possible to capture only thermal radiation from a region as narrow as possible in the surface and to perform the measurement. Alternatively, it is possible to take measures such as uniformly bringing the object into contact with the stage for the heating/cooling in an area as large as possible. Furthermore, in a case of heating by the thermal radiation, the infrared rays from the heat source can be superimposed on the infrared rays radiated from the target object to be measured, thereby introducing an error in the measurement results. In this case, the thermal radiation from the object can be measured after ending or interrupting the thermal radiation from the heat source, however, in a case where such measurement is difficult, an influence of the heat source may be blocked during the measurement by using a shutter-shaped movable member that blocks the infrared rays due to direct reflection from the heat source or reflection from surrounding objects, or the influence from the heat source may be canceled by some arithmetic treatment, machine learning, or the like from the measurement results. Further, a possibility exists that a similar problem occurs in thermal radiation from an inner wall surface or the like of a container accommodating the target object to be measured, other nearby members of the target object to be measured, and the optical system of a measuring instrument itself. In a case where this is a problem, it is possible to take measures such as using the infrared optical system that blocks the thermal radiation from an unnecessary portion as described above, and controlling the heating/cooling so that a temperature of the inner wall surface, the nearby members, the optical system of the measuring instrument, or the like is as low as possible as compared with the surface temperature of the target to be measured, thereby making energy of the infrared rays radiated therefrom sufficiently smaller than energy of the infrared rays radiated from the surface of the target object to be measured.

Figure 6:
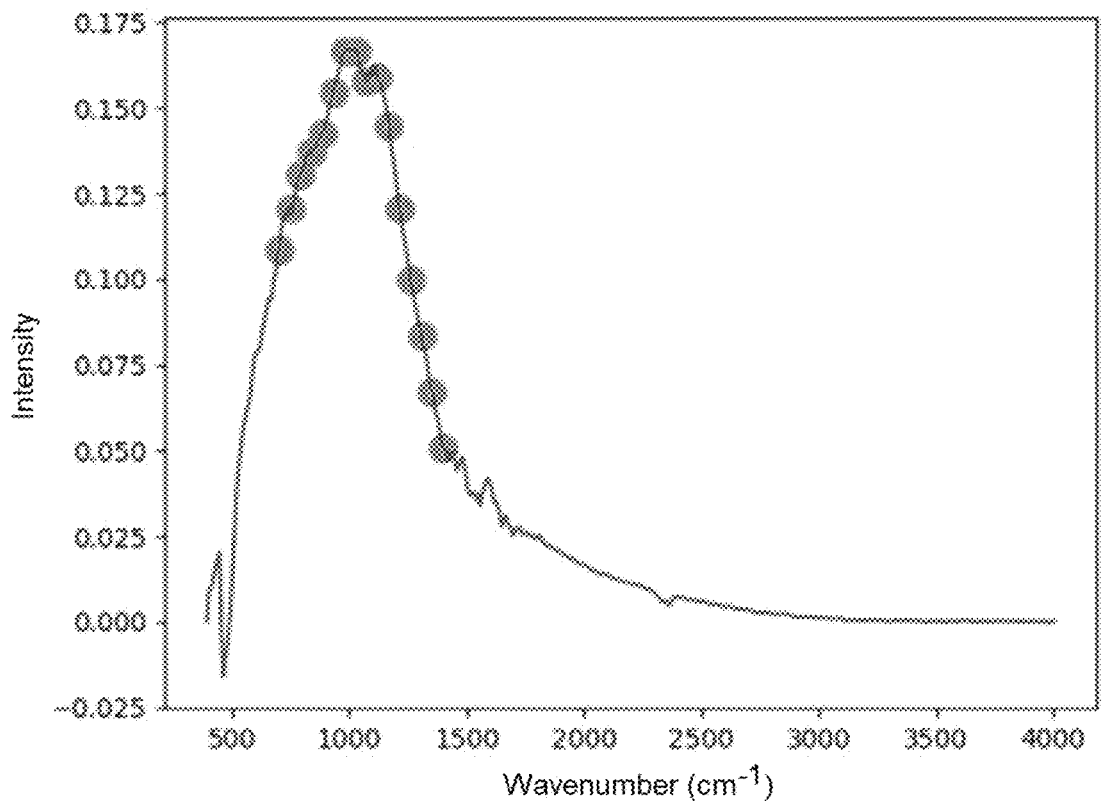
FIG. 6 provides an explanation of a method of selecting feature points on a reference spectrum and a spectrum of the target to be measured.

The reference data and the data of the target to be measured can be identified by processing the intensity data at a large number of wavelength points into the reference data of the discrete wavelengths and the discrete temperatures for each wavelength point at predetermined intervals determined by various factors and using the reference data as the database, and then by comparing the data of the target to be measured of the thermal radiation intensities measured at the discrete wavelengths from the target to be measured with the discrete reference data in the database. Alternatively, on the contrary, the data of the target to be measured of a large number of mostly continuous wavelengths may be compared with the reference data of the discrete wavelengths. FIG. 6 shows an example in which the intensities at the discrete wavelengths on a continuous spectrum is selected, and then measured and recorded. In the example shown in FIG. 6, the continuous spectrum of radiated infrared rays are indicated by a solid line, and intensities at 16 discrete wavelengths are selected as the intensities (the feature values) of points (the feature points) indicating features of the data. The selected feature points are shown as light-colored small discs in FIG. 6. Although slightly horizontally long disks are shown at two points near a peak of the data, it should be noted that each of these disks looks like the horizontally long disk since the two disks are close to each other and are shown in a partially overlapping state. In addition, a horizontal axis of a graph in FIG. 6 is displayed as a wavenumber, however, it should be noted that the wavelength and the wavenumber are in a reciprocal relationship with each other, and thus are treated as being equivalent to each other in the present application.

In FIG. 6, the thermal radiation intensities at 16 discrete wavelengths are used as the feature values, but the thermal radiation intensities may be smaller or larger than the feature values in this example. In general, the identification accuracy increases as the number of wavelengths (the number of feature points) increases, and it is preferable to use four or more wavelengths in a normal case. According to an experiment of inventors of the present application, when the number of wavelengths is increased to about 16 points, identification of conventional materials and objects can be performed with accuracy of 95% or more. Since a limit exists in the wavelength resolution of a measurement device that can be used in the present invention, the accuracy is not improved to any extent by increasing the number of the wavelength points in actual measurement. The identification accuracy can be increased by increasing the number of temperature points during preparing the reference data. In other words, the plurality of temperatures is set within a range of temperatures that can be taken by the target to be measured, the reference data corresponding to these temperatures is prepared, and when the temperature range is more finely divided to increase the number of temperature points setting, the identification accuracy is increased. At that time, when the measurement accuracy of the surface temperature of the material during measuring the reference data (or measurement accuracy of the surface temperature during measurement) is close to a temperature resolution (temperature intervals or increments) in a temperature setting, accuracy of temperature determination can be increased to a degree of the surface temperature.

The accuracy of determination of the reference data is increased when the sample is measured for a plurality of times. It is natural that, when several samples of exactly the same kind are prepared and measured, the accuracy is also increased. Naturally, it has been confirmed that database maintenance of the reference data is very effective for increasing the accuracy.

In the invention of the present application, the accuracy is increased by performing a plurality of measurements on a large number of samples as described above. For this reason, in order to expand discrimination targets and further increase the accuracy, the database including the reference data becomes enormous, and as a result, discrimination time on a computer tends to increase. As a countermeasure for suppressing the increase in determination time, it is possible to use machine learning algorithm, which grasps the features of the data of the sample to be measured and is efficiently found from the database where candidate data is classified as data having similar features in accordance with the grasped features. Accordingly, it has been confirmed that time required for the analysis can be greatly shortened. Specifically, during measuring the reference data, the features (the features of a combination of wavelength-intensity) of the data of the target to be measured are efficiently discriminated by the machine learning, and then the reference data is classified according to the features and accumulated in the database. During measuring the unknown sample, the features of the combination of wavelength-intensity are discriminated and classified by the machine learning, and a candidate having a minimum RMSE is searched while a range is being narrowed down in a classified database, whereby the time can be shortened. For example, by using random forest as the machine learning algorithm, it is possible to realize time reduction of one or more digits. Specifically, the features are quantified from a minimum value, a maximum value and the wavelengths of the intensities, magnitudes of differences between values of a plurality of pieces of data of the adjacent wavelengths, a slope direction of a baseline, and the like, and are classified into groups having the similar features of wavelength-intensity. Then, the data of the target to be measured obtained from the target to be measured is classified using the same method, and the reference data having the similar features and an RMSE value are directly compared from a classification group, and a sample indicating the minimum RMSE value is determined as a solution.

Since the present invention is usually performed in an atmospheric air, the wavelengths of the feature points are preferably selected from a wavelength range in which gas absorption in the atmospheric air is small. In actual measurement, a wavelength region in which water and carbon dioxide are largely absorbed should be particularly avoided. In a case where the measurement is performed in an atmosphere other than the atmospheric air, it is necessary to consider absorption of a gas constituting the atmosphere. In addition, in a case where a possibility exists that another gas is mixed, for example, a gas other than an atmospheric air component is released from the target to be measured or the surrounding objects in a situation where the measurement is performed in the atmospheric air, it is also necessary to consider such gas absorption.

During measuring, recording, and collating these pieces of data (the combination of wavelength-intensity) at the discrete wavelengths and the temperatures in this manner, the wavelengths of the data points in the reference data and the wavelengths of the data points in the discrete wavelengths may be the same or different. In a case where the wavelengths of the data points of both pieces of data that should be compared are different, for example, data interpolation is performed on a wavelength axis, so that a comparison can be performed between the same wavelengths. Hereinafter, it is assumed that both the reference data and the data of the target to be measured are discrete data given at a finite number of points on the wavelength axis, and it is further explained that the wavelengths of the data points in the reference spectrum and the wavelengths of the data points in the spectrum of the target to be measured coincide with one another, but such description clearly does not lose generality.

The comparison between the data of the target to be measured and the reference data is not limited thereto, and to start with, the data is normalized so that the maximum value and the minimum value of the intensities in each piece of data become predetermined values (for example, 0 and 1). In other words, in normalization of the data of the target to be measured and each piece of reference data, in the data, $$I=(I_1, I_2, \ldots, I_i, \ldots, I_n)$$

the intensities $I_1, I_2, \ldots, I_i, \ldots,$ and $I_n$ (n is the number of the data points in each piece of data) for each wavelength, by using a formula below, $$I_i = \frac{I_i - \min(I)}{\max(I) - \min(I)} \quad (1)$$

are normalized to a range of 0 to 1, respectively.

Then, the root mean square error (RMSE) between the data of the target to be measured normalized in this manner and the reference data $$RMSE = \sqrt{\frac{1}{n}\sum_{i=1}^{n}(I'_i - I_i)^2} \quad (2)$$

is obtained. The smaller the RMSE obtained in this manner is, the higher the degree of similarity can be.

Figure 7:
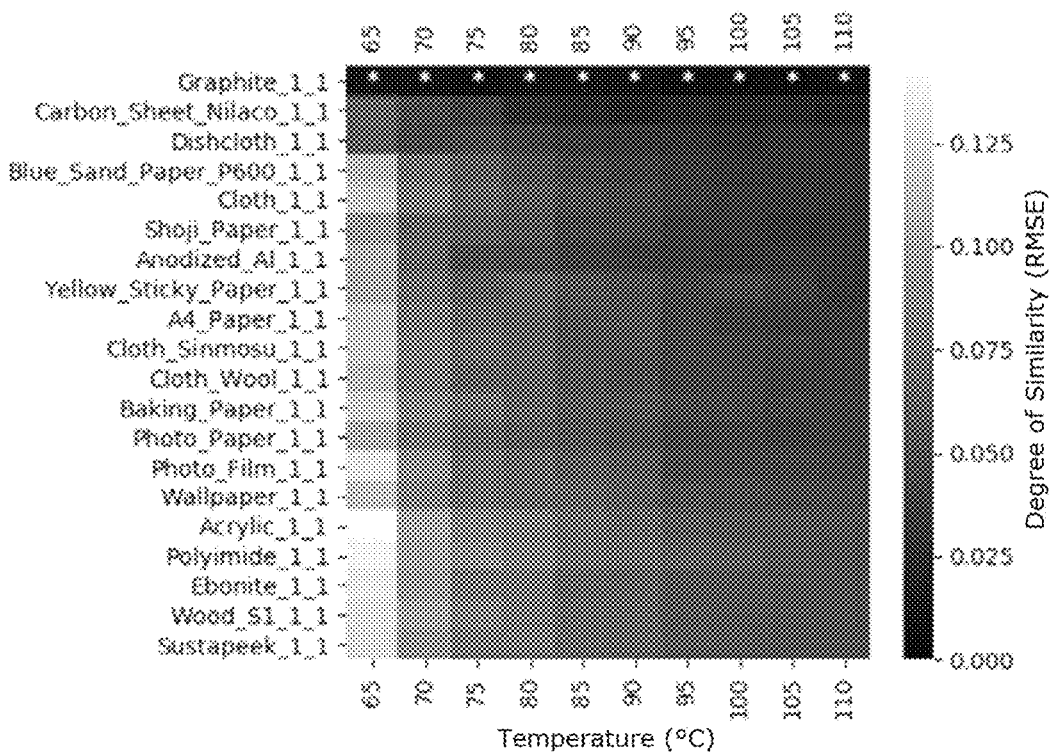
FIG. 7 shows one example in which a graph graphically expresses the material identification of the target to be measured by obtaining the root mean square error between a normalized reference spectrum and a spectrum to be measured.
Figure 8:
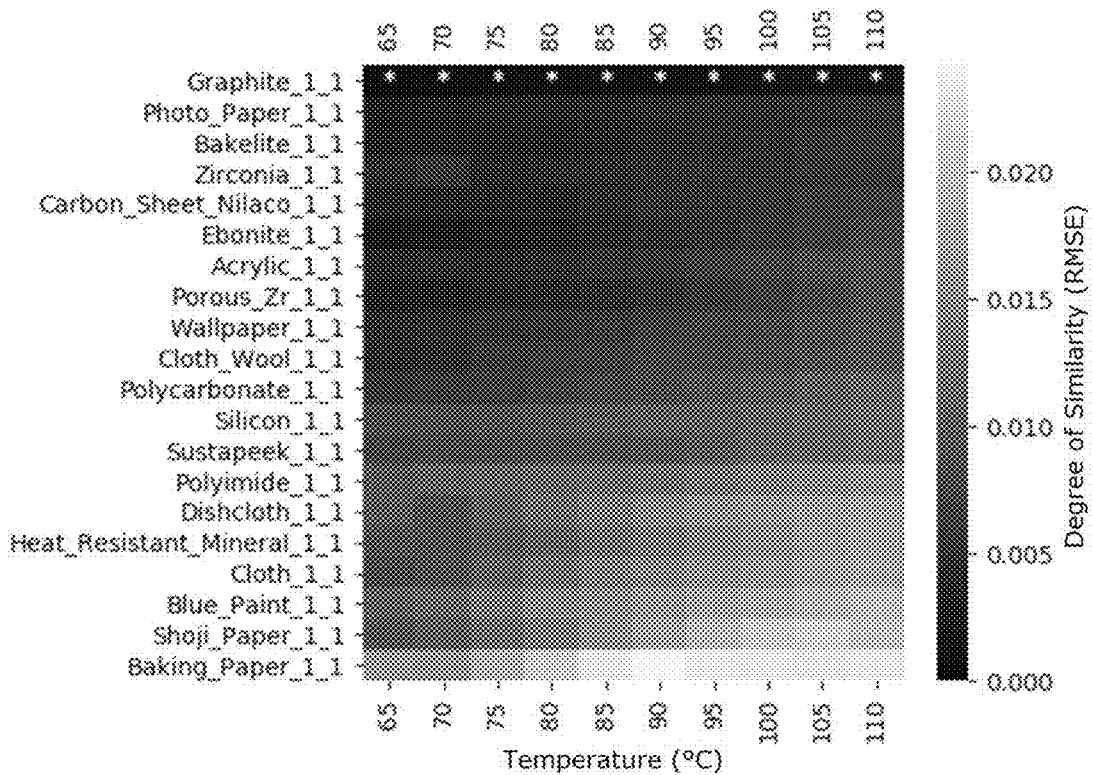
FIG. 8 shows the comparison and identification results with the reference material in a case where graphite is used as the material of the target to be measured in one example of the present invention in a graphed diagram shown in FIG. 7.
Figure 9:
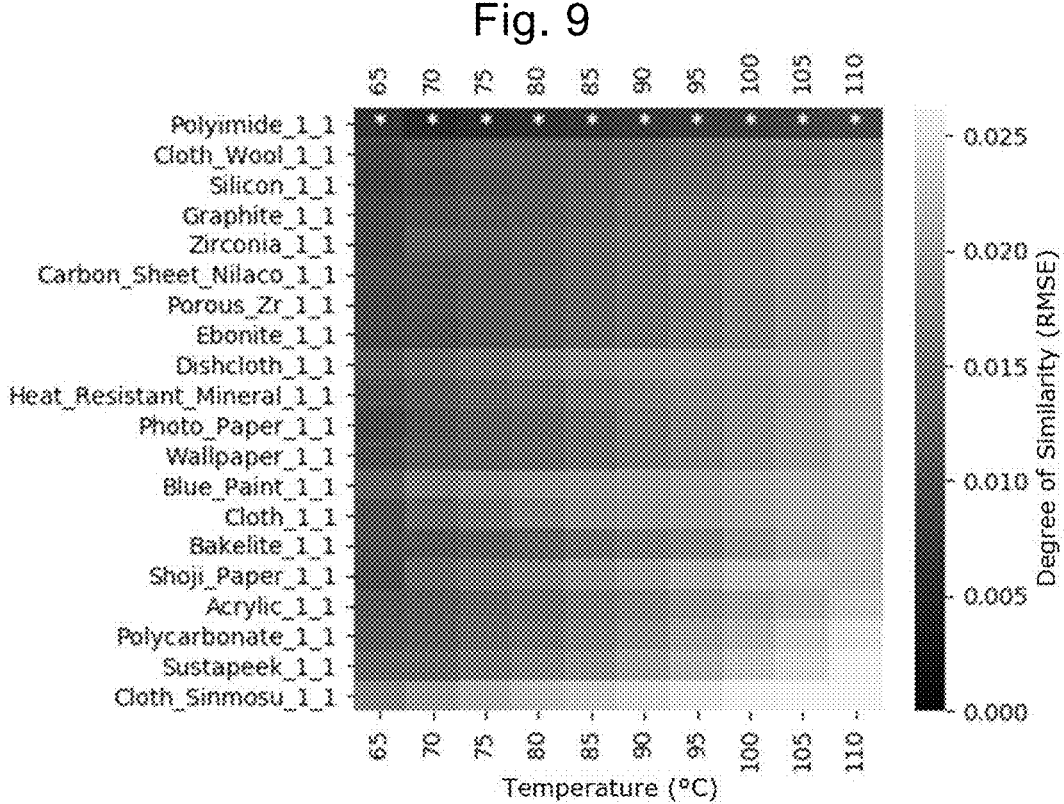
FIG. 9 shows the comparison and the identification results with the reference material in a case where polyimide is used as the material of the target to be measured in one example of the present invention in the graphed diagram shown in FIG. 7.
Figure 10:
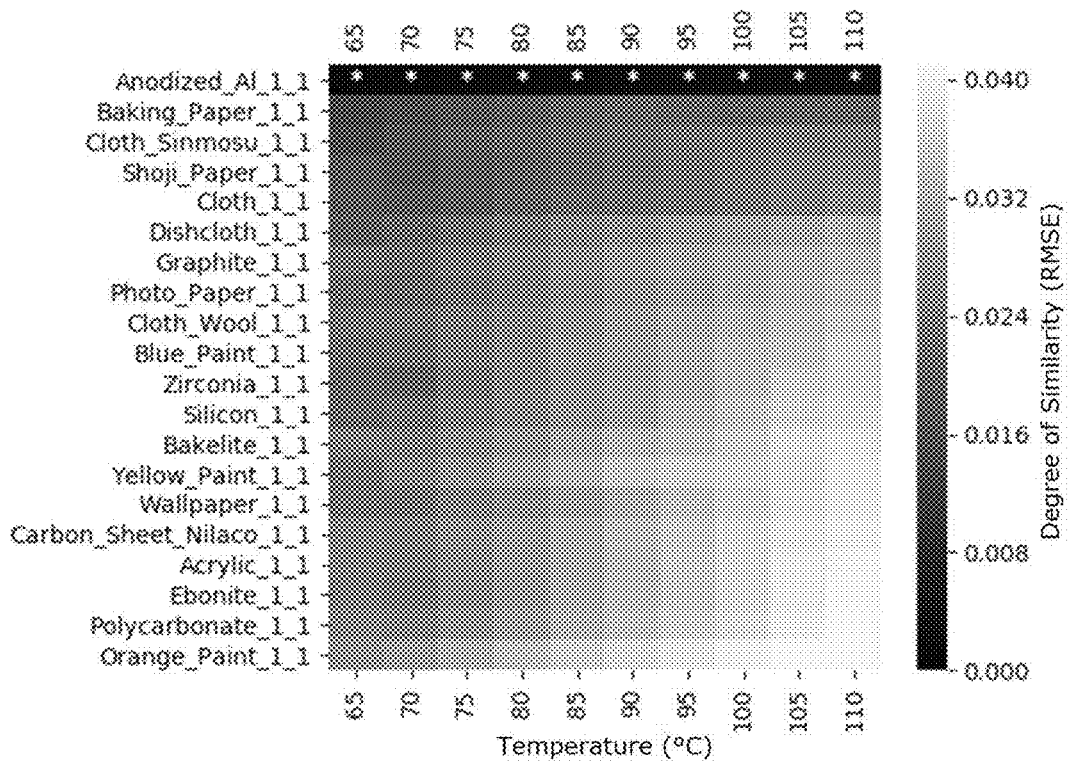
FIG. 10 shows the comparison and the identification results with the reference material in a case where anodized aluminum is used as the material of the target to be measured in one example of the present invention in the graphed diagram shown in FIG. 7.
Figure 11:
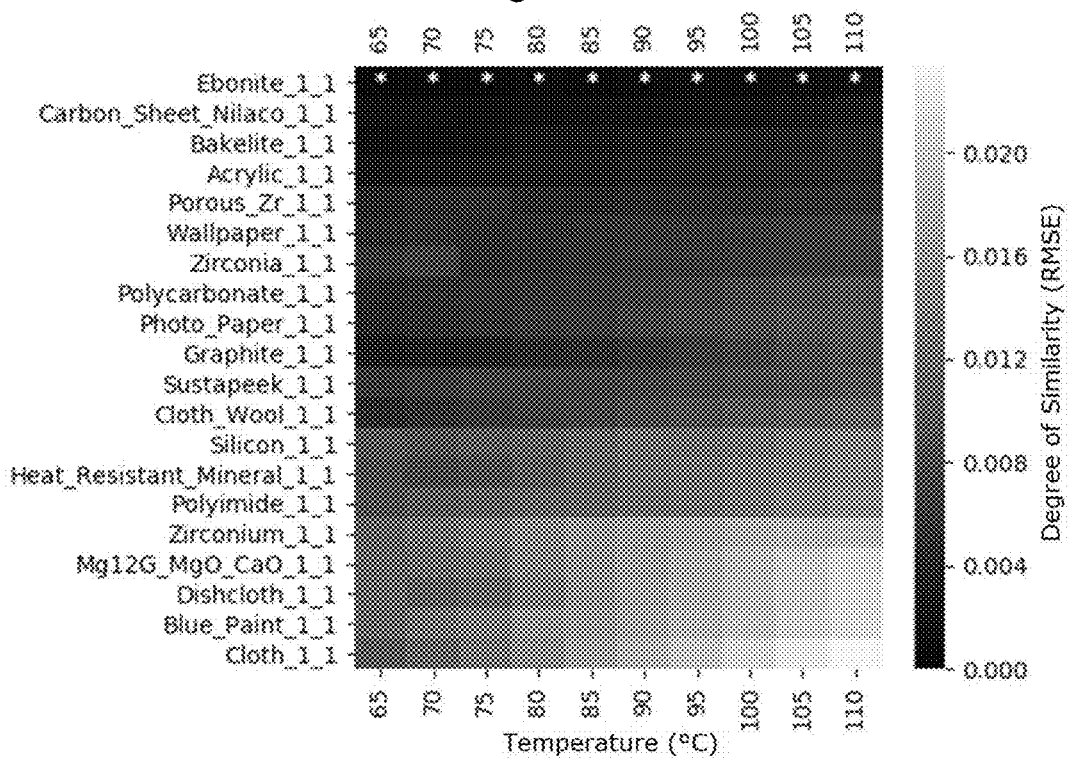
FIG. 11 shows the comparison and the identification results with the reference material in a case where ebonite is used as the material of the target to be measured in one example of the present invention in the graphed diagram shown in FIG. 7.
Figure 12:
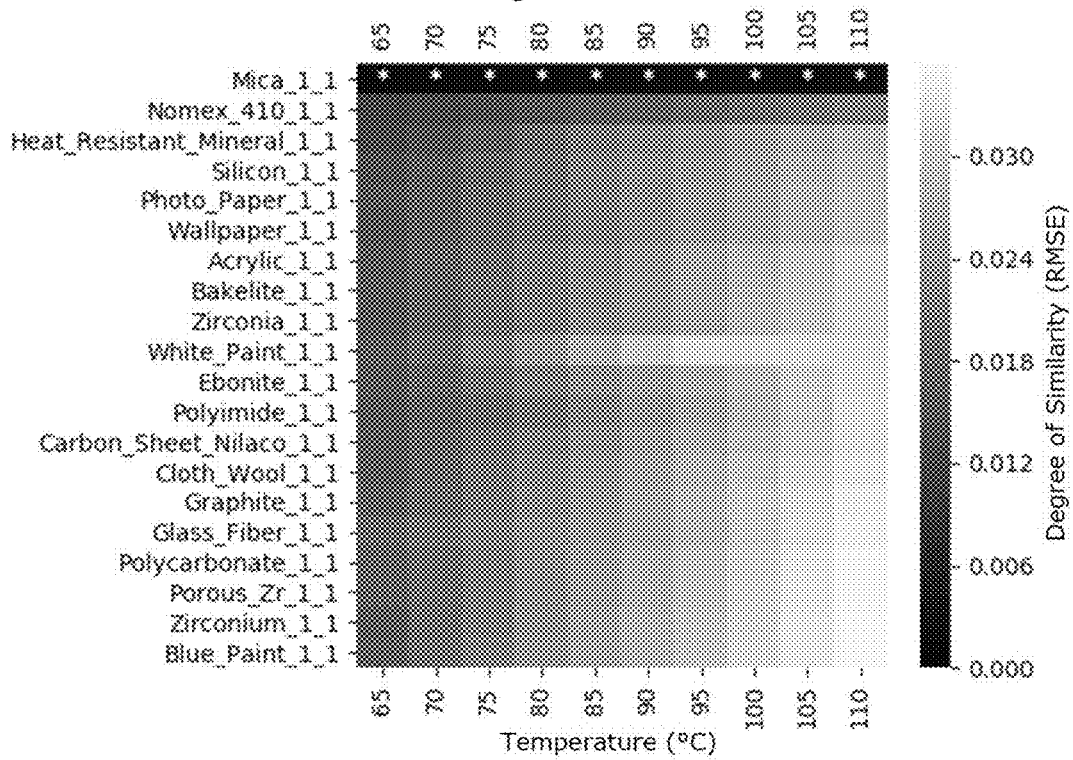
FIG. 12 shows the comparison and the identification results with the reference material in a case where mica is used as the material of the target to be measured in one example of the present invention in the graphed diagram shown in FIG. 7.
Figure 13:
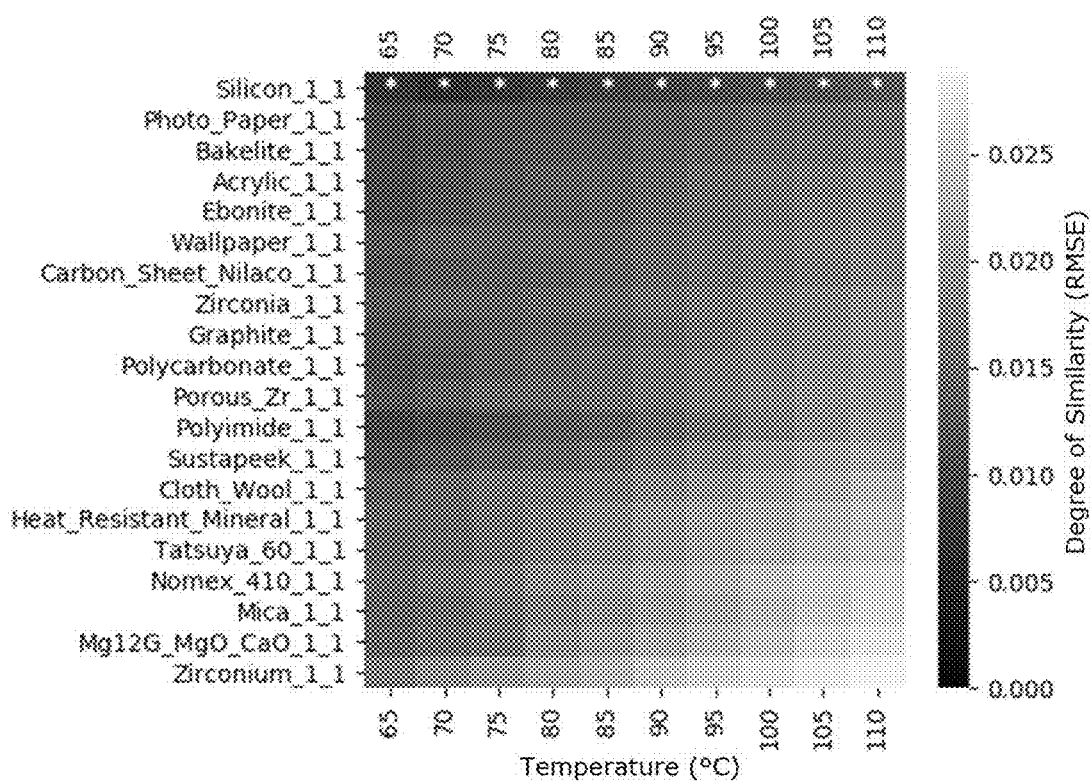
FIG. 13 shows the comparison and the identification results with the reference material in a case where silicon is used as the material of the target to be measured in one example of the present invention in the graphed diagram shown in FIG. 7.
Figure 14:
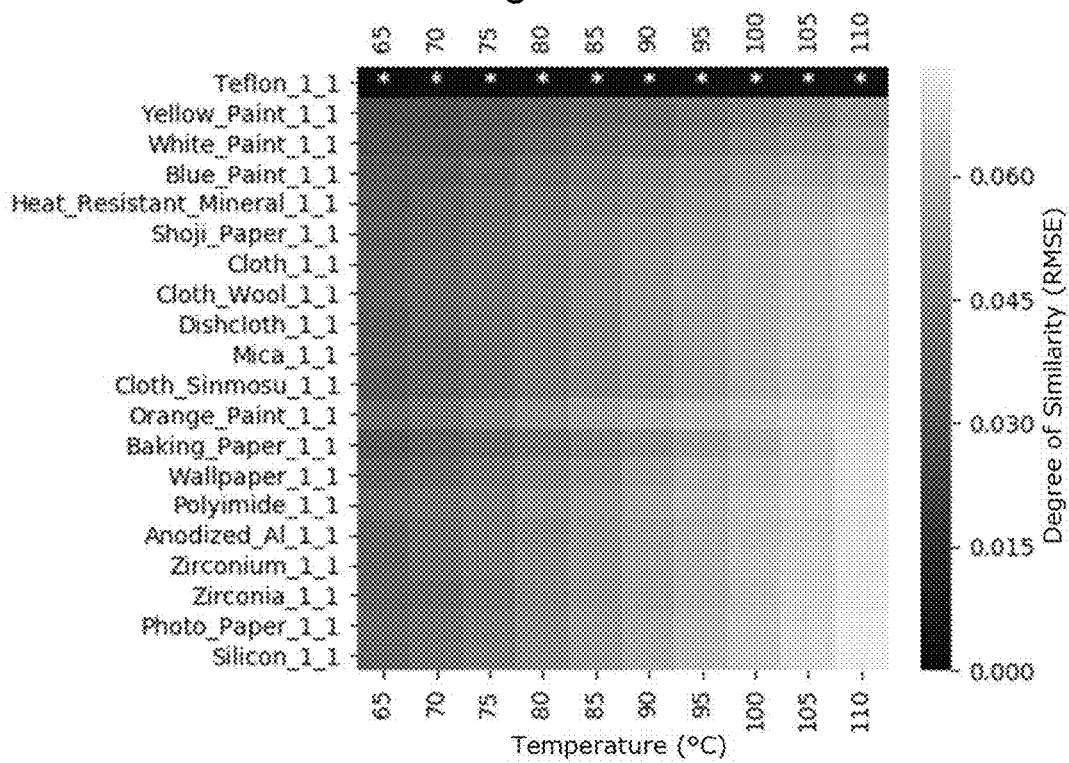
FIG. 14 shows the comparison and the identification results with the reference material in a case where Teflon (registered trademark) is used as the material of the target to be measured in one example of the present invention in the graphed diagram shown in FIG. 7.
Figure 15:
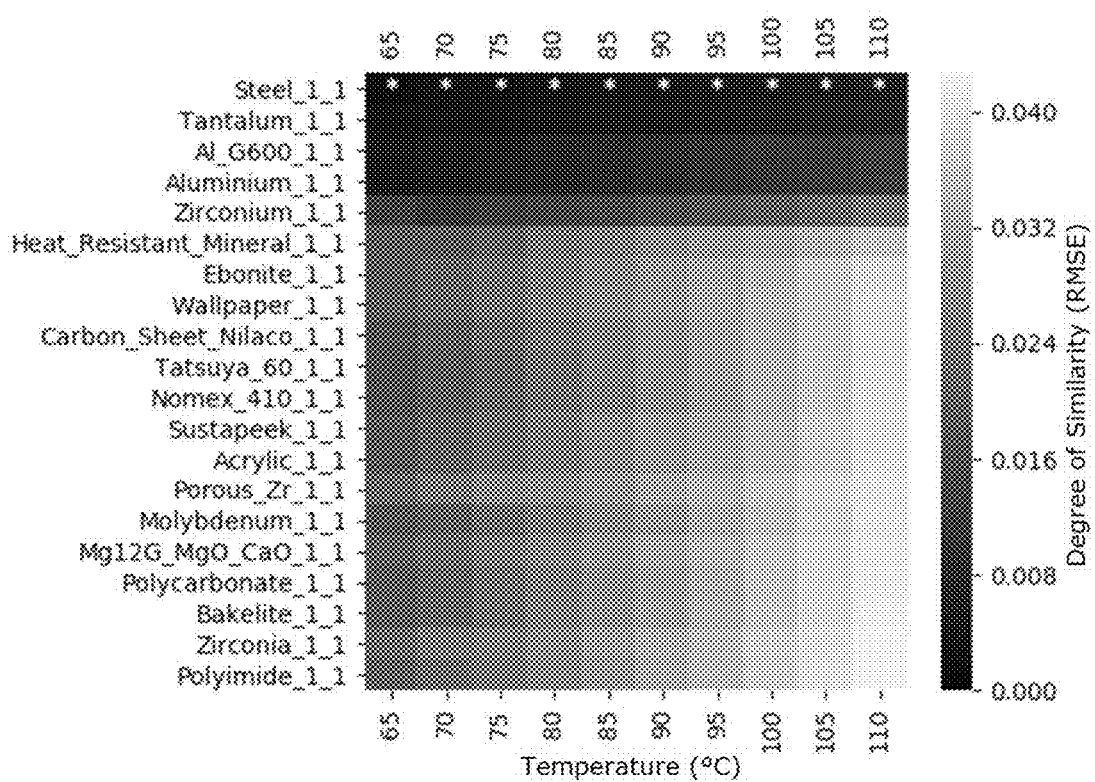
FIG. 15 shows the comparison and the identification results with the reference material in a case where steel is used as the material of the target to be measured in one example of the present invention in the graphed diagram shown in FIG. 7.
Figure 16:
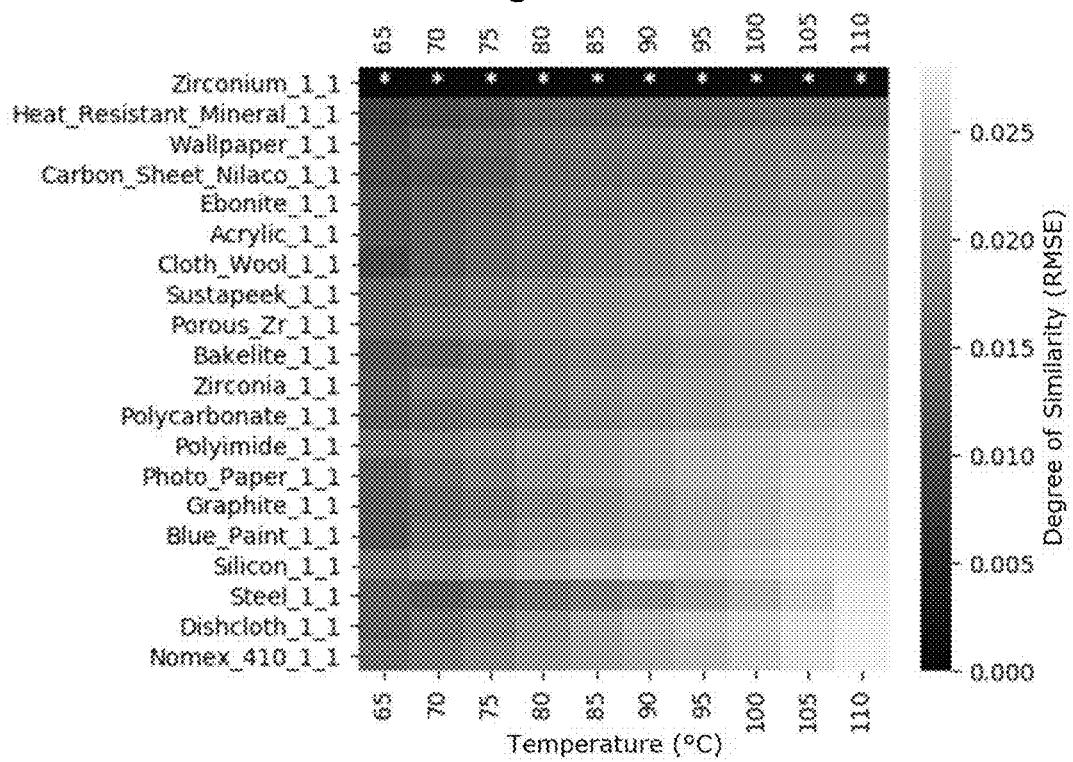
FIG. 16 shows the comparison and the identification results with the reference material in a case where zirconium is used as the material of the target to be measured in one example of the present invention in the graphed diagram shown in FIG. 7.
Figure 17:
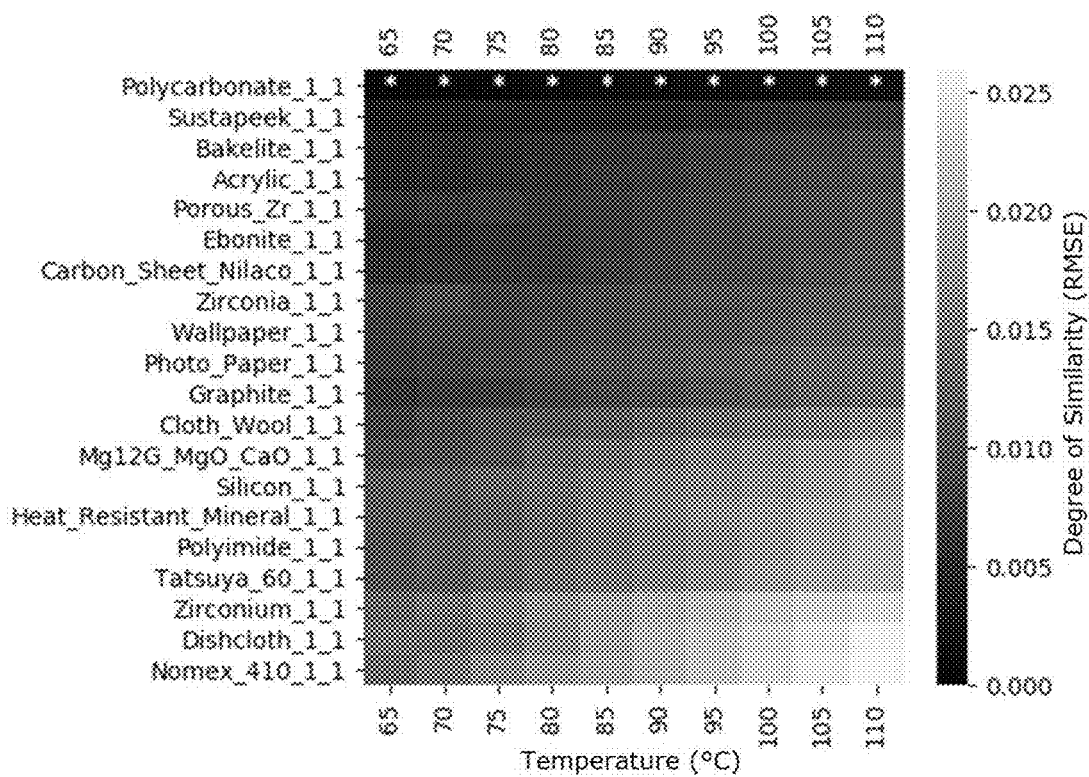
FIG. 17 shows the comparison and the identification results with the reference material in a case where polycarbonate is used as the material of the target to be measured in one example of the present invention in the graphed diagram shown in FIG. 7.

FIG. 7 shows an example of a graph graphically representing the material identification of the target to be measured. The identification is obtained by RMSE between the reference data and the data of the target to be measured in which each intensity is normalized. In FIG. 7, the temperature of a certain target to be measured is set at an interval of 5° C. between 65 to 110° C., the data of the target to be measured at each temperature is compared with the reference data obtained at these temperatures from 20 kinds of materials (the reference materials) shown on a vertical axis, the RMSE is obtained, and concentration of an intersection portion between each material and temperature is shown so as to be the concentration corresponding to a value of RMSE of the intersection portion shown in a concentration chart at a right end. As can be seen, at any temperature, since the RMSE between the reference data and the data of the target to be measured from graphite is minimum, the target to be measured can be identified as being made of graphite. Here, the reference material having the minimum RMSE at the temperature is indicated by writing an asterisk (*) at the intersection portion having the minimum RMSE for each temperature. The vertical axis in FIG. 7 defines an order of the reference materials such that the RMSE is small, that is, the materials having large degrees of similarity are on a top. In addition, the reference material having the minimum RMSE may be different depending on the temperature based on the material of the target to be measured and measurement conditions at various places. In such case, for example, the reference material having the minimum average value of RMSE over all temperatures can be the material having the maximum degree of similarity, that is, the material that should be identified may be the material of the target to be measured. Alternatively, another evaluation criterion may be set, for example, a weighted average in which a large weight is assigned to a temperature at which a difference for each material is likely to appear instead of a simple average of RMSE at all temperatures.

Advantages of this method are discussed in comparison with the prior art. In an existing analysis method such as infrared absorption spectroscopy, in order to focus on the molecular vibration having a sharp structure with respect to the wavelengths, it is necessary to measure almost the continuous spectrum and determine the material by looking down an entire image. However, in a method of the present invention, such steep emission spectrum structure due to all the molecular vibration or phonons is not only used for the discrimination. The present invention also discriminates by using an overall thermal radiation spectral intensity change in a slow but wide wavelength range. The intensity change is derived from changes in the Planck radiation when changing the temperature and from changes in conductivity of the material (such as plasma oscillation due to thermal excitation) (which has a large influence in particular in a case of semiconductors). For this reason, as compared with the method such as the absorption spectroscopy, an advantage exists in which the discrimination can be performed with high accuracy when the number of the wavelengths to be used is overwhelmingly small. Further, since a light emission (the thermal radiation) of the target to be measured itself is used, a great advantage exists in which the light source for irradiating the sample with light is unnecessary (that is, no light source need to be used for the measurement, or the light source can be omitted).

Here, just in case, the present invention is compared with a specific prior art disclosed in Non Patent Literature 5 to further clarify a difference therebetween. In the present invention, the thermal radiation from the target object to be measured is measured at the plurality of wavelengths, and these measurement results are compared with a reference set, so that a combination of the most suitable substance and the temperature is obtained. The reference set consists of a set of thermal radiation intensities at the plurality of wavelengths from a plurality of kinds of substances at the plurality of temperatures measured in the same manner for reference. It is noted that, when a substance constituting the surface of the object is known in advance, it should be compared with only the set of thermal radiation intensities for the substance in the reference set, and on the contrary, when the temperature is known, it should be compared with only the set of thermal radiation intensities for the temperature in the reference set. On the other hand, in the method disclosed in Non Patent Literature 5, the thermal radiation intensities from the target object to be measured is measured at the plurality of wavelengths, and the temperature of the object is obtained from these intensities by using the newly proposed algorithm as described above.

As can be seen from the above, the method of Non Patent Literature 5 is common to the present invention in that the thermal radiation intensities from the target to be measured are measured at the plurality of wavelengths, but the temperature is determined by using only the thermal radiation intensities at the plurality of wavelengths from the target to be measured without performing comparison with the reference set in the present invention. In this respect, the procedure thereof is completely different from that of the present invention. Due to this difference, the material constituting the surface of the substance of the target to be measured is not identified by the method of Non Patent Literature 5, and how the method described therein should be modified in order to perform this identification is not suggested at all.

In addition, in the method of Non Patent Literature 5, a considerably complicated algorithm is used instead of performing comparison with the reference set for temperature identification. Accordingly, high data processing performance is required to process the data of the target to be measured. Further, in a prior method explained for the multi-wavelength analysis method near a beginning of a section "Description of Embodiments", values of the temperatures or the emissivities are not uniquely determined, and ambiguity and arbitrariness always exist in principle. In the present invention, comparison with each set of thermal radiation intensities in the reference set can be performed by a direct and simple calculation such as the RMSE, and when the kinds of materials accumulated in the set increase, the number of times of comparison increases only linearly with the kinds of the materials, so that a calculation load is not so high. In the present invention, both the temperature measurement and the material identification of the target can be performed using a simple and clear method of performing comparison with the database, and the solution is uniquely determined in principle. It is natural that, please note that further improvement such as an increase in measurement accuracy can be achieved by performing additional processing such as the machine learning in the present invention.

Furthermore, in Non Patent Literature 5, as a specific example of the measurement, the thermal radiation intensities at 1600 K or a higher temperature is measured, and a wavelength for measuring the radiation intensities is also mainly within a visible band. This respect is an essential difference from the method of the present invention that mainly uses the thermal radiation due to the molecular vibration or phonon vibration in a mid-infrared band region, which thereby increases the accuracy of substance identification. In addition, only six kinds of materials of the target to be measured exist. Accordingly, only a few of special materials withstanding such extremely high temperature are verified, and thus generality thereof is not necessarily reliable in Non Patent Literature 5. In this respect as well, it can be said that Non Patent Literature 5 differs greatly from the present invention. The present invention has been widely verified for various materials (metal, ceramic, semiconductor, organic material, composite material therefore, gas material, and liquid material) having greatly different characteristics from one another as shown in examples of the present application.

In addition, regarding the comparison of the degrees of similarity between the data of the target to be measured and the reference data, one aspect using a method (the RMSE method) that is determined exclusively based on the root mean square error has been explained, but a method that can be used for the comparison of the degrees of similarity is not limited thereto in the present description. To start with, a definition of the degrees of similarity is not limited to the RMSE, and any degree of similarity beginning with a cosine degree of similarity can be used. Next, important points on the spectrum are extracted by the machine learning (a feature extraction by the machine learning), and the degrees of similarity can be evaluated from the features. For example, it is possible to extract spectral feature values as a continuous value or a discrete value, to evaluate the degrees of similarity, and to use the feature values for discrimination of a substance, a temperature, and a state by using a variational autoencoder or the like. Furthermore, each spectrum may be expressed in a bit string of 0/1 by using a machine learning method for extracting the feature by 0/1, such as the variational autoencoder capable of hashing (can be expressed by 0/1) the feature. As a result, a degree of similarity search technique using a hash can be used, and the degree of similarity search can be performed at a high speed. In addition to these methods, naturally various degree of similarity search techniques for vectors having continuous values and discrete values can be used.

Further, the present invention can also be applied to a case where the target to be measured is not one of the plurality of candidate materials for the material identification of the target to be measured, but the target to be measured is a mixture of two or more of these candidate materials. In other words, it is possible to correspond to a mixture spectrum by considering a spectrum of a mixture including the plurality of materials as a synthesis of the spectrum for each material. At this time, either a linear or nonlinear synthesis method can be used as the synthesis of the spectrum. Further, in order to understand which single substance spectrum is synthesized, this can be reduced to the combinatorial optimization problem, and a set of reference data having high degree of similarity can be selected by using an optimization method using the machine learning such as a black box optimization method as a solution thereto. Then, various solving methods for the combinatorial optimization typified by a quantum annealing method can be used for further speeding up.

To summarize comparison results between Non Patent Literature 5 explained above and the present invention, the present invention has advantageous features such as (A) being able to identify the material because the measurement is mainly in the infrared band and molecular/atomic vibration is measured; (B) being able to be used not only at a high temperature but also in the vicinity of the room temperature; and (C) being a simple and clear comparison method based on comparison with the database and not depending on an elaborate analysis method.

It is noted that, the temperature of the target to be measured should be kept as constant as possible while one piece of data of the target to be measured (wavelength-intensity data) is measured, but as explained above with reference to FIG. 7, the identification accuracy can be increased by changing the temperature of one target to be measured in a plurality of ways, measuring the data of the target to be measured for each of the plurality of temperatures, and comparing the data of the target to be measured with the reference data. Also in this case, the identification accuracy is increased by increasing the number of temperature points measured. Although depending on a resolution of the sensors to be used and other measurement conditions, sufficient accuracy was obtained by performing measurement at a temperature of about 1 to 3 points within a temperature range of about 50 to 70° C. in the experiment conducted by the inventors of the present application. In addition, a difference from Non Patent Literature 5 is obvious in that the material can be identified by performing the measurement using a temperature change in the vicinity of the room temperature, and the temperature in the vicinity of the room temperature can be measured.

In addition, when the data of the target to be measured is measured at the plurality of temperatures, the temperatures may be known or not be known. This is because the data of the target to be measured can be compared with the reference data in the database when the temperature is unknown.

Further, a case will be considered, where the temperature of the material of the target to be measured is constant but the temperature itself is unknown during the measurement of the data of the target to be measured. The thermal radiation intensity is proportional to a product of $I(\lambda, T)$ and the emissivity $\varepsilon(\lambda)$ in the Planck's radiation formula. Thus, the spectrum changes when the temperature changes. Further, a variable I in the Planck's radiation formula has an influence on a shape of a wide wavelength range of the spectrum, and the emissivity $\varepsilon$ results in a finer, steeper spectral shape difference due to material differences. In other words, the spectral shape of the thermal radiation varies depending on both the material and the temperature. Accordingly, the temperature of the target to be measured can be obtained by knowing the thermal radiation intensities at the plurality of wavelengths. It is natural that, both the material and the temperature of the target to be measured can be obtained simultaneously.

This will be explained more specifically below. When the temperature of the material of the target to be measured is different, the spectral shape of the electromagnetic waves such as the infrared rays radiated from the material changes depending on both the Planck's radiation formula and the emissivity of the material. Accordingly, when the data of the target to be measured (the wavelength-intensity data) from the material at a constant temperature wherein the temperature itself is unknown is compared with the reference data, it is natural that the degrees of similarity of the reference data corresponding to the same material as the material of the target to be measured are high. However, among the pieces of reference data corresponding to the same material, the reference data obtained at a temperature different from a material temperature at which the data of the target to be measured is obtained provides lower degrees of similarity than the reference data obtained at the same temperature. In other words, a gentle envelope curve of the thermal radiation changes according to $I(\lambda,T)$ of the Planck's radiation formula by measurement while changing the temperature, and this effectively works in the determination performed using, for example, the RMSE described above, so that the determination can be performed with high accuracy. Accordingly, in a case where results from a degree of similarity measurement described above, that is, the results of comparing the data of the target to be measured with the reference data under the conditions that the temperature during measuring the data of the target to be measured is a certain single temperature, are expressed in a form of FIG. 7 (here, the horizontal axis of the graph represents the temperature associated with each piece of reference data subjected to the comparison), not only the degrees of similarity greatly change along a vertical axis direction (a material axis direction) of the graph, but also the degrees of similarity greatly change in a horizontal axis direction (a temperature axis direction). From the results, when the reference data having the maximum degree of similarity with the data of the target to be measured is selected, the identification results are given that the material and the temperature of the target to be measured are the material and the temperature associated with the reference data. Alternatively, when the plurality of pieces of the reference data is selected in the descending order of degrees of similarity, identification candidates, that is, a list of the plurality of materials and temperatures associated with a plurality of selected pieces of the reference data is given as the identification results of the material of the target to be measured.

Here, for the measurement of the reference data and the data of the target to be measured, for example, Fourier transform infrared spectroscopy (FTIR) can be used although not limited thereto. As another non-limiting example, a device for determining the multi-wavelength intensity data of incident thermal radiation can be used by using a configuration (multi-wavelength sensors, multi-band sensors) in which a plurality of sensors having sensitive wavelength bands shifted from one another is arranged. In this case, a wavelength region useful for material identification or temperature identification in the thermal radiation is divided into a plurality of narrow wavelength regions, and radiation intensities in each wavelength region are obtained. At this time, in general, the identification accuracy is improved as the number of divisions of the wavelength region is larger. According to the experiment of the inventors of the present application, it is necessary to divide the material into at least 4 small wavelength regions in order to perform practical identification, and when the material can be divided up to about 16 regions, it is possible to identify a conventional material with accuracy of about 95%. Further, a small wavelength region resulting from the division above, in which the radiation intensities are obtained, is preferably selected from a wavelength region in which the gas absorption (water vapor, carbon dioxide, and the like) in the atmospheric air is small.

Further, the infrared sensor that can be used to detect the thermal radiation is not particularly limited, as long as it can be incorporated in a device capable of measuring wavelength dependency and the spectrum of the thermal radiation intensities, and can be appropriately selected within a range meeting various measurement environments such as the temperature of the target to be measured and various requirements such as required measurement accuracy. Although the sensor is not intended to be limited thereto, examples of the specific sensors that can be used include a mercury cadmium telluride (MCT) detector, a triglycine sulfate (TGS) detector, a DTGS detector in which hydrogen ions of the TGS detector are deuterated, and the like. In addition, the measurement was performed by using the MCT detector in the examples. The measurement was also performed by using the DTGS detector.

Further, in a case where the temperature of the target to be measured can be known, when the data of the target to be measured (the combination of wavelength-intensity) is compared with the reference data (the combination of wavelength-intensity) accumulated in the database, a collation with only the reference data corresponding to the temperature of the target to be measured can be performed. By doing so, it is possible to eliminate the reference data that is small in need of collation in advance, and thus, particularly in a case where the number of pieces of the reference data is enormous, collation time can be shortened, and probability of performing erroneous identification is reduced. However, when the measurement can be performed by changing the temperature of the target to be measured, the material can be identified with higher accuracy as explained above by performing the measurement at the plurality of temperatures and comparing the measured temperatures with the reference data. It is natural that, these temperatures are not necessarily known when measuring the wavelength-intensity of the target to be measured, and these temperatures can be simply different from one another. The material is identified by comparison with the reference data, however, in a case where an identified material is different depending on the temperature of the target to be measured, the identification accuracy is increased as compared with a case of measurement at a single temperature, for example, by performing the determination such as taking a majority decision of the identification results for each temperature, in which the material having the highest degree of similarity is the final identification result.

The plurality of temperatures in the reference data can be those required to realize the material identification and/or the temperatures with required accuracy. These temperatures depend on heat resistance of a used material, accuracy and sensitivity of the sensor, and the like, but in the examples below, the material could be identified with high accuracy by performing the measurement at 5° C. intervals within a range of 65° C. to 110° C.

It is noted that, the temperature of the target to be measured itself considerably changes depending on, for example, thermal resistance between the target to be measured and a heating stage, thermal conduction of the target to be measured itself, a contact state between the target to be measured and the heating stage, and the like, and specifically, a measurement error of about 5° C. may occur. Accordingly, when the high accuracy is required for the material identification and the temperature identification, it is necessary to accurately know a relationship between the temperature of the heating stage and the temperature of the target to be measured.

In addition, when only the material identification of the target to be measured is performed, identification with high accuracy can be achieved only by preparing the reference data at the 5° C. intervals described above. However, in a case where the temperature of the target to be measured is to be identified with high accuracy, it is desirable to eliminate the influence of the error described above and prepare the reference data measured at intervals narrower than 5° C. (for example, 1° C. intervals). Alternatively, it is also possible to use the reference data after the reference data is obtained at a temperature that is not actually measured by the interpolation with a relatively small error from the reference data at the plurality of temperatures in the vicinity. Alternatively, the reference data corrected by using the Planck's radiation formula can be obtained and used.

Further, in a case of the same substance, thermal radiation spectrum varies depending on a surface state such as roughness of the surface and a surface structure on a nano/micrometer scale. In order to cope with this, it is conceivable to systematically collect materials made of the same substance but having various surface roughnesses and nano-microstructures, to acquire the reference data for all of the materials, and to accumulate the reference data in the database. However, in a case where too various surface structures are possible and cannot be easily handled, for example, through learning an influence of the surface structures and the roughness on the thermal radiation spectrum by the machine learning, the material identification for which the reference data is not actually obtained can also be realized. Alternatively, when the machine learning is not performed, the reference data at the temperature that is not actually measured may be interpolated with the relatively small error from the reference data at the plurality of temperatures in the vicinity as to be explained below. For this interpolation, in addition to simply using the reference data measured in the vicinity, general features of a variation of the radiation spectrum according to the Planck's radiation formula and temperature can also be utilized.

Further, as another case of the identification of the material for which the reference data has not yet been actually obtained, the present invention can also be applied to a case where the reference data for each of the materials is a mixture of two or more materials selected from a plurality of known materials as candidates for the material identification of the target to be measured. Furthermore, the present invention is similarly applicable to a case where a target to be identified can be one of the plurality of candidate materials but is not necessarily guaranteed to be one, and can be a mixture of the plurality of materials selected from the candidate materials. For example, when an unknown material is mixed with the plurality of materials of a material A and a material B, it is assumed that the spectrum can be expressed by a superposition of spectra of A and B, and it is considered that a measured spectrum of the unknown material can be expressed by some linear combination or non-linear combination of spectra in the data set that has already been measured, or a combination having both features. In other words, this method can replace the spectrum of the unknown material with a problem of obtaining a combination of spectra that can be best represented in an input spectrum by a linear (nonlinear) coupling of the spectra (the number of the spectra is arbitrary) in a piece of constructed reference data. In addition, the reference data obtained from the spectrum that is obtained by combining any number of spectra in the reference data in this manner is also referred to as combined reference data hereinafter. In addition, all pieces of the combined reference data can be prepared in advance for comparison, but rather, it is also possible to generate and provide only those needed at a necessary timing by calculation and the like on the spot. As a result, it is possible to reduce a capacity for storing the combined reference data, which tends to be a huge amount, and to reduce a calculation amount and calculation time for the preparation thereof. Furthermore, for example, identification of a material that does not yet exist or a material to be produced from limited reference data is also possible by using the combined reference data.

Furthermore, in order to understand which single substance of the reference data is a spectrum synthesis, it can be reduced to the combinatorial optimization problem, and a method using the machine learning can be applied. Specifically, as a solution to the combinatorial optimization problem, the black-box optimization method, a simulated annealing method (a quantum annealing method or the like), various solution methods for the combinatorial optimization can be used, and the discrimination can be sped up. In particular, when considering linear bonding, a mixing ratio can also be expected in addition to the kinds of materials mixed. In other words, when the discrimination of the mixture is simply performed by a method below, the number of combinations becomes enormous and it can be difficult to realize the method in the present invention. Specifically, a set Rc of the combined reference data in which 1 to n pieces of the reference data are selected and combined from a set R of n pieces of the reference data is considered (in addition, when only one piece of reference data is selected, a piece of corresponding combined reference data is an original piece of reference data itself). In this case, the number of elements of the set Rc of the reference data is often considerably large. Furthermore, considering that the mixing ratio of the single material to be a basis of the reference data is changed in many stages, the number of the elements of the combined reference data set becomes enormous. Accordingly, when the combined reference data having the highest degree of similarity with the data of the material of the target to be identified is determined from the set of the reference data Rc, when the determination on degree of similarity of a round-robin formula is performed, the number of comparison times for the determination on the degree of similarity becomes enormous, which is not realistic in many cases. Therefore, the number of comparison can be greatly reduced, and the determination can be completed within a realistic time by applying the solving methods for the combinatorial optimization problem such as the black-box optimization method known to those skilled in the art. Further, no preparation of an enormous number of the combined reference data is required in advance, yet can be calculated only when needed, and thus this is also helpful for the time reduction.

Further, each piece of the data is normalized through linearly converting the multi-wavelength intensity data by using Formula (1) such that the maximum value and the minimum value become predetermined values (for example, 0 and 1), but the normalization does not necessarily use this formula in the explanation above. For example, in a case where noise on a spike is placed near the peak of the measured data, since the maximum intensity of the data is assumed to be a value larger than the true maximum intensity, the intensities of the normalized data become excessively small when the normalization is performed by using Formula (1), and a possibility exists that an error evaluation performed thereafter will be adversely affected. In order to avoid or reduce an influence of such noise, other kinds of normalization can be performed. Although the present invention is not intended to be limited thereto, for example, the influence of the noise and device drift can be eliminated or reduced by obtaining the measurement results of the plurality of pieces of data obtained by measuring the data for a plurality of times, averaging the measurement results, and then performing normalization (here, a plurality of obtained sets of the measurement results can be examined, and can be averaged after eliminating an inconvenient measurement result such as an excessive noise being added thereto and obviously unnatural data (unnatural jumps of the intensities, and the like)), obtaining feature values from the intensities at a plurality of adjacent wavelengths (for example, an average of three intensities measured at a nominal wavelength of the feature values and wavelengths before and after the nominal wavelength is defined as the intensity of the data at the nominal wavelength) instead of adopting the measured values of the data at a single wavelength when extracting individual feature values from the data, scaling the intensity data such that an average value of the intensities (although it is the same thing, it refers to a total/integral value of the intensity data) in the entire wavelength region of the target to be measured or a partial section thereof becomes a constant value, and the like. Further, although a linear conversion is performed in Formula (1), for example, the portion can have a larger influence on the comparison results by giving a large weight to a specific portion (a specifically measured value range, a wavelength range, and the like) in the multi-wavelength intensity data.

More generally speaking, a main purpose of the normalization performed here is to address a fact that multi-wavelength intensity data for reference and the multi-wavelength intensity data of the target to be measured should be identical when the same material is measured at the same temperature, but they do not completely match due to various factors. In other words, in order to remove the various factors described above, at least one of the multi-wavelength intensity data for reference and the multi-wavelength intensity data of the target to be measured is converted according to some rule, and then both pieces of the intensity data after conversion are compared with each other, so that an error evaluation value (for example, the root mean square error according to Formula (2)) between both pieces of the data in the same material and the same temperature can be minimized or close to the minimum.

Further, a comparison of the intensity data after normalization, that is, the calculation of the degrees of similarity is performed by obtaining the root mean square error between the intensity data as shown in Formula (2) in the above explanation, but other kinds of comparison can also be performed. For example, it is also possible to perform the comparison by obtaining an absolute value of data intensity for each wavelength and taking an average thereof although not limited thereto. In addition, for comparison of other kinds including this, the normalization mentioned in the above explanation of the method using the RMSE can be essential. However, the normalization is not necessarily required in the comparison using the machine learning and the like in some cases. For example, a case where the feature values reflecting the shape of the spectrum are compared corresponds to a latter case.

For example, it is possible to extract a feature portion from a set of collected data and intensities by using the variational autoencoder and the like, which is a kind of neural network. Further, the feature values of the spectrum can be represented by 0/1 (each spectrum can be represented by a bit string of 0/1), and the degree of similarity search can be executed at a high speed by using a binary variational autoencoder and the like. This degree of similarity search method can be used instead of the RMSE method to determine the substance, the temperature, and the state. In the method of the present invention, values of some points of the spectrum are used, yet can also be extracted as some feature values, and the feature values can be converted into not only the continuous value but also the discrete value or a binary value.

Further, this method can be applied to a classification method for improving efficiency and speed by using the determination involving a large amount of reference data described above. Further, it can also be used for classification of data of measurement. In other words, it is also possible to perform rough classification prior to final discrimination based on the RMSE of the unknown material by using this classification method, and then perform the RMSE discrimination on a small number of pieces of the reference data of a classification category to shorten time required for the discrimination. Alternatively, in parallel with the RMSE method, it is also possible to increase the accuracy of the discrimination by performing the discrimination while comparing with each other or incorporating both results.

Speeding up of spectrum degree of similarity search by the variational autoencoder can be reduced as how the important points are extracted from the spectrum. Accordingly, although some data points are extracted for the discrete wavelengths in the spectrum, the data points at important wavelengths can be extracted by using the machine learning method based on the autoencoder. It is natural that, the feature extraction is not limited to the autoencoder, and various machine learning methods for the feature extraction may be used to extract the feature. Further, although values of some discrete data points of the spectrum are used, some feature values may be extracted and used instead. At this time, as the feature values, it may be converted into not only the continuous value but also the discrete value or the binary value. Then, a method of calculating the degrees of similarity at a high speed when the feature values are obtained can be used. For example, the similarity search technique using the hash can be used. It is natural that, in addition to the above, various similarity search techniques for vectors having continuous values and discrete values can be used.

In the explanation above, during the measurement of the thermal radiation from a reference sample for obtaining the reference intensity data for a combination of a specific material and a specific condition (for example, a case where the temperature is 90° C.) where there are conditions such as temperature, it is assumed that the combination of the material and the conditions is combined into one piece of reference data by performing the number of measurements of the multi-wavelength intensity data of the thermal radiation only once or performing processing such as averaging the measurement results for a plurality of times when the measurements are performed for a plurality of times. However, the present invention is not limited to limiting the reference intensity data to the combination of the specific material and the specific conditions to one.

When thermal radiation data (the reference data in this case) is measured for the same material under the same conditions such as the temperature, by introducing variations in measurement errors into the measurement results, the obtained reference data is not necessarily the same for each measurement. Accordingly, a set of the reference data can include a plurality of pieces of mutually different (or possibly different) data obtained by measurement of the same material under the same conditions, and the measurement results for identifying the material and/or the temperature, that is, the comparison with the data of the target to be measured can be performed. Such measurement/comparison is performed, the reference data is arranged in the descending order of degrees of similarity, a piece of higher order data is viewed, and the majority decision is taken for the material and/or the temperature, whereby the material and/or temperature that occupies the majority is identified as the material and/or temperature of the target to be measured. In a case where such comparison is made, and in a case where it is assumed that a variation in the measurement of the same material under the same conditions is not extremely large, the reference data corresponding to the measurement of the same material and the measurement at the same temperature is ranked higher than the reference data arranged in the order of degrees of similarity. Accordingly, when the majority decision as described above is taken, the reference data corresponding to the same case as the material and/or the temperature of the target to be measured has high degrees of similarity. As a result, when such majority decision is taken, the identified material and/or the temperature will be mostly accurate. Furthermore, an influence of variations, errors, and the like in obtaining the individual piece of reference data is reduced by the majority decision as described above. Consequently, in a case where the plurality of reference data for the same material and the same conditions is prepared, it can be expected that the identification accuracy is higher than that in a case where only one piece of reference data is prepared for each case.

Further, all the targets to be measured are solid in the examples of the present application, yet the present invention can be equally applied to any of the targets to be measured being the gas, the liquid, or a mixed object thereof from the principle of the present invention described above. In addition, although there is a mesophase that takes an intermediate state between the solid, the liquid, and the gel macroscopically existing as the solid but microscopically having a structure in which the liquid and the solid are mixed, these are all regarded as the solid in the present application. Accordingly, it should be noted that the term "the target object to be measured" in the present application includes all phases and states of the solid, the liquid, and the gas, and the mixture thereof. For the gas, the gas and plasma also emit light when the temperature is high, and this can also be referred to as the thermal radiation. The same applies to the liquid.

It is noted that, when the present invention is performed, it is common to stop a temperature rise to a temperature that does not impart an irreversible change to the material of the target to be measured or the like, but the present invention is not limited thereto.

As another aspect of the present invention, it is also possible to determine a degree processing in the processing of a material or an object. For example, as is typical in processing usually performed in a field of food processing, when a material that is altered, decomposed, or the like at the high temperature is heated, a spectrum of electromagnetic waves such as the infrared rays radiated therefrom changes not only by the surface temperature but also by reflecting an alteration due to a reaction or the like between the plurality of materials initially included, a change of a material that was originally one into another substance due to phase separation, or the like. Such alteration and decomposition are affected not only by the temperature but also by heating time, a heating profile, and a heating means (heating with radiation heat, heating with hot air, microwave heating, and the like). Furthermore, raw materials, shapes, and sizes of the target to be subjected to heat treatment, and variations in pretreatment also affect progress of the alteration, the decomposition, and the like. A similar situation occurs not only in food processing but also in determination of a state of drying/curing of coating, plastic, or the like. Conventionally, it has not been easy to realize such evaluation of the progress or the like of the processing in the non-contact manner, and it is greatly useful for quality control of a production line if possible. In one aspect of the present invention, the fact is utilized that not only the temperature but also a physical or chemical change of the material, a component composition accompanying evaporation of a volatile component, the surface structure, and the like are changed by the progress of the processing such as modification of the material (hereinafter, it is simply referred to as the processing). Specifically, multi-wavelength data of the thermal radiation is measured for each processing stage and recorded in the database as the reference data, and it is possible to determine how far the processing of the material or the like of the target to be measured has progressed by comparing the data with the reference data. The reference data is recorded from the measurement of the thermal radiation from the material or the like during the heat treatment for which the processing stage is to be determined.

Furthermore, it is also possible to identify the normality of this kind of processing, that is, to determine whether the processing has progressed normally or has not progressed normally due to some causes (or whether a product obtained after the processing has been processed normally or is defective). In this case, when a workpiece is identified as a normal workpiece by collation with the normal workpiece reference data accumulated in the database, the processing is identified as normal, and when a workpiece is not identified as the normal workpiece, the processing is identified as abnormal. Alternatively, the reference data obtained from a typical defective material (a composition of components, a surface state, and the like) that can be generated from the abnormal progress of processing is also accumulated in the database, and the thermal radiation data obtained from an object in the processing process or after processing is compared with the reference data in the database, so that it can be determined whether the processing is normal or abnormal, that is, whether the processing is proceeding normally (or whether the normal processing is finally performed). In addition, when the target to be measured is identified as the reference data of the typical defective material accumulated in the database at this time, information useful for estimating what kind of abnormality has occurred in the processing process is obtained. Alternatively, in a case where the comparison cannot be made with the material in a middle of the processing or a final result or with any defective material, the material is identified as "other defective material". In this case, it is estimated that a situation not accumulated in the database (in many cases, some abnormality that occurs only infrequently or has never occurred before) has occurred. This can be applied to quality control of very various industrial products.

Furthermore, the present invention can be applied not only to monitoring of the progress of the processing during processing, but also to checking of a temporal change such as deterioration during use and storage of an arbitrary material or object. More specifically, the thermal radiation data is acquired at a certain time point (at an initial state such as at a time of manufacturing, at a time of shipment, or at a time of start of use, or at any other time) based on the reference data, and thereafter, the thermal radiation data is similarly acquired at an arbitrary time point (after long-term storage, at a time of periodic inspection such as after use for a certain period of time, at a time of determining whether or not to reuse a used product, and at a time when the abnormality is suspected) at which the temporal change is desired to be examined, and the thermal radiation data is collated with one another, and whether or not the temporal change has occurred can be inspected. Further, it is also possible to acquire, as the reference data, data in which the same material or the object has undergone aging or aged deterioration, or data in which the same material or the object has fallen into various abnormal states, and compare the data with the aging or aged deterioration data and/or the abnormal state data at a time of comparison above, thereby examining a degree of the aging or aged deterioration, what kind the abnormality has occurred is or how severe the abnormality is, and the like. In other words, instead of identifying the unknown material, an inspection is performed on whether or not a change from an original material has occurred in a target material or object, or how much and/or what kind of change has occurred under conditions that the original material is the same kind of material but a possibility exists that it has changed due to some factors (time, environment, use, and the like) in this application.

It is natural that, in measuring, recording, and comparing the data (the combination of wavelength-intensity) at the discrete wavelengths and temperatures in the same manner as already described in the present application, the wavelengths of the data points in the reference data and the wavelengths of the data points in the discrete wavelengths when measurement is performed at an arbitrary time point may be the same or different. In a case where the wavelengths of the data points of both pieces of data to be compared are different, for example, the data interpolation is performed on the wavelength axis, so that the comparison can be performed between the same wavelengths. Further, the measurement of the reference data and the measurement at any time point may be performed at a single temperature or at the plurality of temperatures. In addition, a material or an object for which the reference data is to be acquired can be the same as a material or an object for which a presence or an absence of subsequent aging, aged deterioration, abnormal state, or the like is to be examined. Alternatively, the material or the object may not necessarily be the same as the material or the object for which the reference data is to be acquired, and may have sufficiently close thermal radiation characteristics. Furthermore, all the materials and objects that can appear as objects for inspection and the like may not be sufficiently close to any one of the materials and objects for which the reference data is to be acquired in terms of the thermal radiation characteristics. More specifically, when at least a part of a collection of materials or objects that can appear as an object of inspection or the like is a mixture of the plurality of materials or objects for which the reference data is to be acquired, elements of such mixture and a mixing ratio of these elements can be obtained as explained above. As a result, it is possible to obtain an effect of suppressing an increase in an amount of pieces of the reference data to be prepared, for example, in a case where components of the object, a ratio thereof, or the like continuously change in a progress of processing, the temporal change, or the like, or in a case where a plurality of kinds of changes can occur simultaneously. Further, examples of the material and object include, but are not limited to, parts, foods, works of art, and exhibits.

In addition, only solids are exemplified as the target to be measured, but the present invention is not limited thereto and can also be applied to liquids and further to the gases. Concerning gases, the Planck's radiation formula is also applicable to the molecular vibration, that is, since the Planck's radiation formula changes the intensities of each radiation at a specific wavelength of a gas in an envelope manner, the principle described above is also applied to gases. In addition, when the target to be measured is a liquid, particularly a volatile liquid, it is necessary to avoid a situation in which radiation from vapor generated from the liquid is measured in a form of being mixed with radiation from the liquid itself. For this purpose, for example, it is possible to rapidly remove the vapor while causing a carrier gas that does not absorb the infrared light, such as nitrogen gas to flow on a liquid surface, to measure radiation in a state in which the vapor is not interposed through a container wall or the like wherein absorption or the like is small in a wavelength region of the target to be measured at a time of measuring the radiation, or to compensate an influence of the absorption after similar measurement in a case where an absorption spectrum of the container wall or the like is known.

As explained above, it is possible to determine which of the candidate materials measured in advance is the material of the object only by measuring the intensities of the thermal radiation at a relatively small wavelength. Furthermore, when the temperature of the object at the time of measuring the data of the target to be measured is unknown, the temperature of the target to be measured can also be easily identified when the temperature at the time of measuring the reference data is known. In the present invention, since the information being measured is effectively used by utilizing an overall change over a gentle but a wide wavelength range due to the radiation intensity curve by the Planck radiation when the temperature is changed and the radiation from the plasma vibration by a thermal excitation carrier, the high accuracy can be realized when the number of wavelengths for measuring the intensities of the thermal radiation is reduced. Further, for a material that changes due to the heat treatment processing or the like, the progress of the heat treatment processing progressing or the like can be determined from the thermal radiation data of the material.

EXAMPLES

Hereinafter, the present invention will be explained in detail with reference to the examples, but it should be noted that the examples are presented only for understanding of the present invention and examples are not intended to limit the present invention.

The data (the wavelength-intensity data) of the thermal radiation from 18 kinds of materials of the target to be measured was measured at 5° C. increments from 65° C. to 110° C., and this was compared with the reference data obtained by measuring 50 kinds of reference materials at the same temperature range and the temperature increments in examples below. In the present example, the MCT detector is used as the infrared sensor for detecting these intensities as described above. FIGS. 8 to 25 show the graphs in which the comparison results of both pieces of data are arranged in the same manner as in FIG. 7 for the top 20 kinds of reference materials in the descending order of degrees of similarity (an ascending order of the RMSE). It is noted that, since the reference material indicating the minimum RMSE can be different depending on the temperature (that is, not all of intersections marked with asterisks are necessarily present in the top row of the graphs in FIGS. 8 to 25), strictly speaking, arrangements in the vertical axis direction of the reference material on the graphs are in the ascending order of an average value of RMSE over an entire temperature as described in the explanation of FIG. 7.

Here, as the 18 kinds of materials of the target to be measured, specifically, graphite, polyimide, anodized aluminum (Anodized_Al), ebonite, mica, silicon, Teflon (registered trademark), steel, zirconium, polycarbonate, tantalum, aluminum, molybdenum, acrylic, alumina ($Al_2O_3$), Nomex (registered trademark) 410 sheet (Nomex_410), Bakelite, and cloth of 100% cotton were used. FIGS. 8 to 25 show the comparison results between the reference material and these materials of the target to be measured in such order. Among the 50 kinds of reference materials, materials appearing as the top 20 kinds of reference materials in at least one of FIGS. 8 to 25 in comparison with any one of the materials of the target to be measured are as follows: acrylic, gray colored electrodeposition coated alumite (Anodized_G-600) (Al G600) provided by Kaimeishindo co., ltd, an alumina plate (2-305-01) ($Al_2O_3$ 98) with a purity of 98% provided by AS ONE CORPORATION, $Al_2O_3$ ($Al_2O_3$ Trio Ceramic) with a purity of 96% provided by Trio Ceramics Co., Ltd., aluminum, Anodized M6 Black alumite (Anodized Al), Bakelite, baking paper, blue paint, carbon sheet (model number C-07346) (Carbon Sheet Nilaco) with a purity of 99.5% supplied from Nilaco Corporation, cloth (98% cotton, 2% polyurethane) (Cloth), cloth 100% (cotton) (Cloth Sinmosu), cloth wool, dishcloth, ebonite, glass fiber, graphite, insulating sheet HIPSKH (inorganic mineral fiber) (heat-resistant mineral) supplied from Misumi, Magnesia Mg 12G (MgO 99.6%, CaO 0.1%) (Mg 12G MgO CaO), which is a ceramic product supplied from NIKKATO CORPORATION, mica, molybdenum, Nomex (registered trademark) 410 sheet (Nomex 410), orange paint, photo paper, polycarbonate, polyimide, porous zirconium (porous Zr), shoji paper, silicon, steel, SUSTAPEEK, tantalum, Tatsuya 60 sandpaper No. 60 (Tatsuya 60), Teflon (registered trademark), olefin-based wallpaper, white paint, yellow paint, zirconia, and zirconium. In FIGS. 8 to 25, abbreviations shown in parentheses at an end of each reference material name listed above are written. The same abbreviations are used in FIG. 7.

As is clear from the comparison and identification results shown in FIGS. 8 to 25, in one example of the present invention, the data of the target to be measured from 18 kinds of various materials at temperatures in increments of 5° C. between 65° C. and 110° C. and 50 kinds of reference data at the same temperatures were normalized using Formula (1), respectively, the RMSE at each temperature was determined from both normalized data using Formula (2), and a reference material with the smallest RMSE was taken as an identification result at that temperature. This achieved very good identification accuracy. In other words, for a large number of very diverse kinds of materials of the target to be measured, specifically the graphite (FIG. 8), the polyimide (FIG. 9), the anodized aluminum (FIG. 10), the ebonite (FIG. 11), the mica (FIG. 12), the silicon (FIG. 13), Teflon (registered trademark) (FIG. 14), the steel (FIG. 15), the zirconium (FIG. 16), the polycarbonate (FIG. 17), the molybdenum (FIG. 20), the acrylic (FIG. 21), the alumina (FIG. 22), Nomex (registered trademark) 410 sheets (FIG. 23), the Bakelite (FIG. 24), and the fabric (FIG. 25), the materials could be accurately identified at all temperatures. Also, for two materials of the target to be measured as exceptions, the tantalum (FIG. 18) was erroneously identified as Al_G600 and the aluminum at 70° C. and 75° C. of 10 measurement temperatures, respectively, yet it can be seen that the degree of similarity when the tantalum is used as the reference material is still very large. Further, the aluminum (FIG. 19) was also erroneously identified as the tantalum only at 70° C., yet it can also be seen that the degree of similarity when the aluminum is used as the reference material is also very large. In such case, the identification accuracy can be secured by quantifying the identification results for the plurality of temperatures, averaging the results, and the like to make comprehensive determination.

Figure 18:
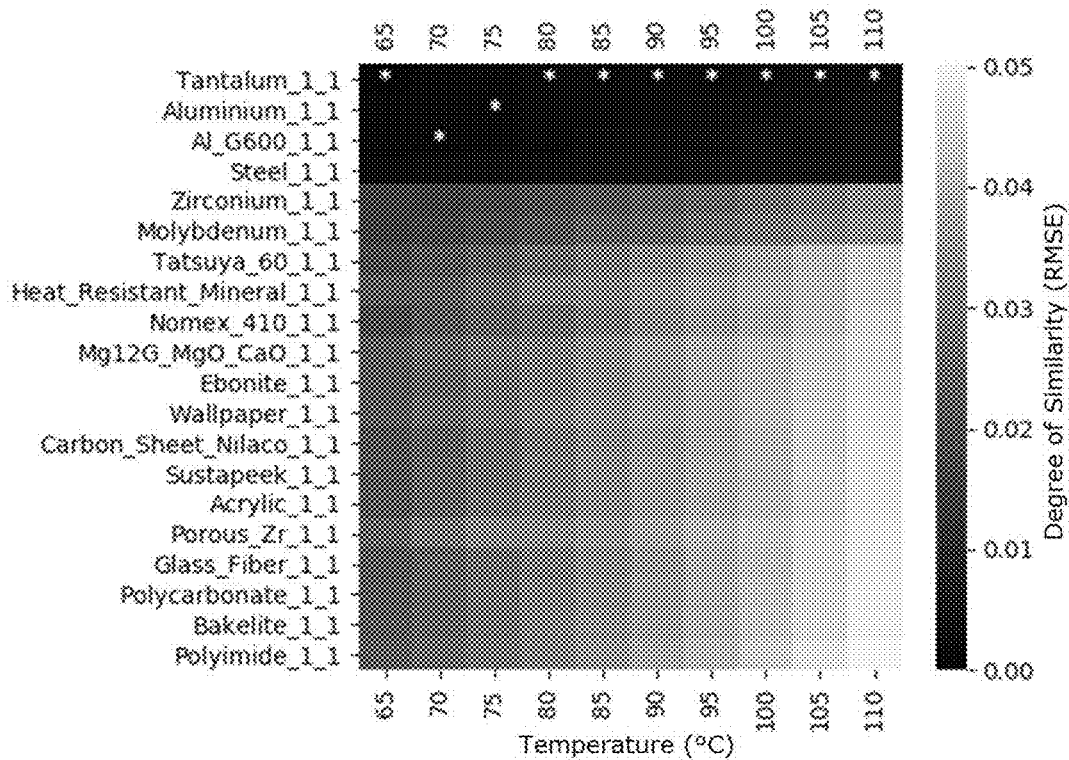
FIG. 18 shows the comparison and the identification results with the reference material in a case where tantalum is used as the material of the target to be measured in one example of the present invention in the graphed diagram shown in FIG. 7.
Figure 19:
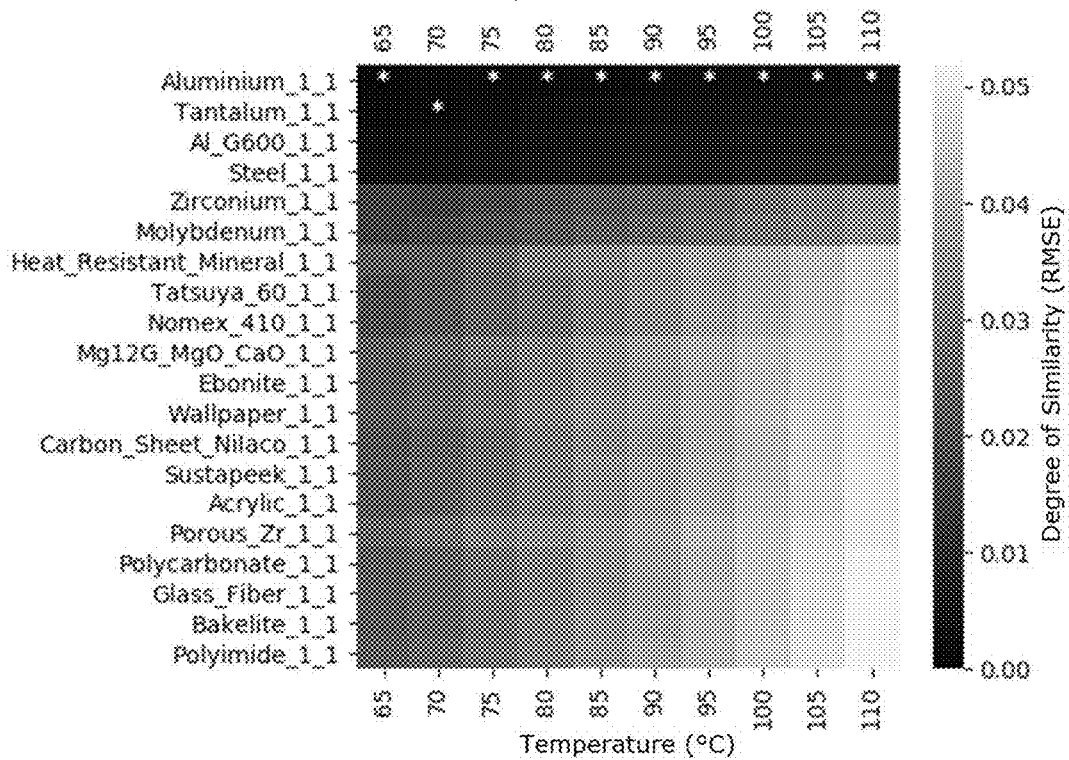
FIG. 19 shows the comparison and the identification results with the reference material in a case where aluminum is used as the material of the target to be measured in one example of the present invention in the graphed diagram shown in FIG. 7.
Figure 20:
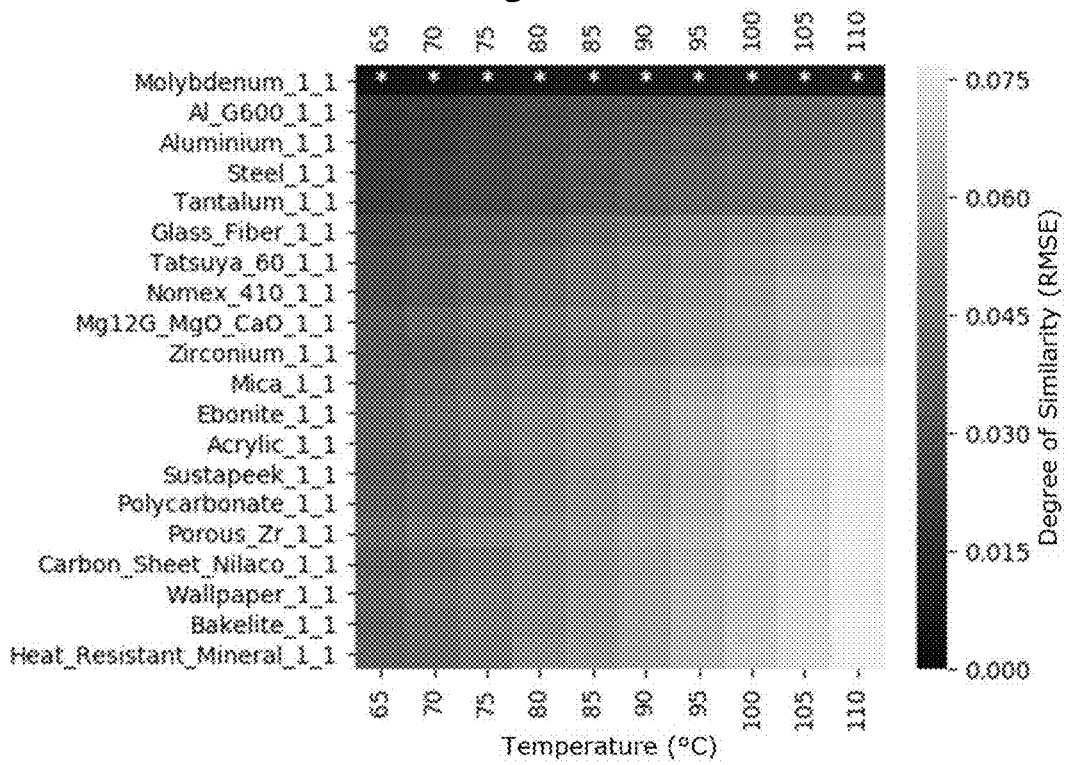
FIG. 20 shows the comparison and the identification results with the reference material in a case where molybdenum is used as the material of the target to be measured in one example of the present invention in the graphed diagram shown in FIG. 7.
Figure 21:
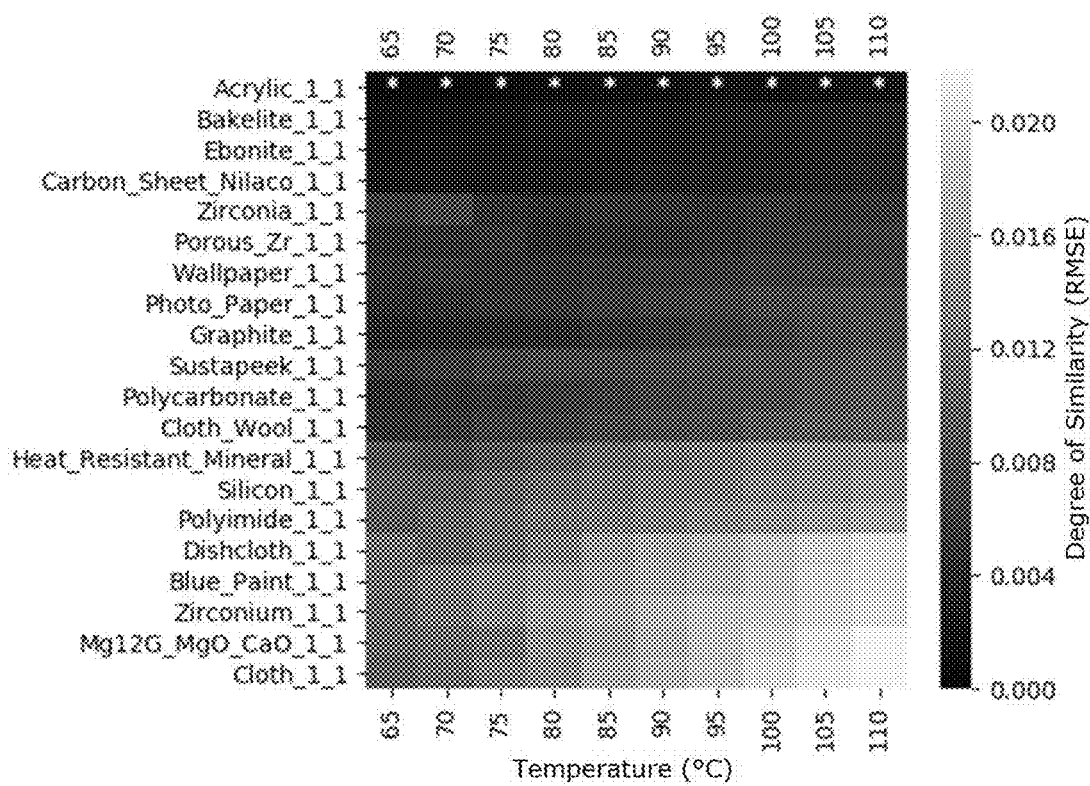
FIG. 21 shows the comparison and the identification results with the reference material in a case where acrylic is used as the material of the target to be measured in one example of the present invention in the graphed diagram shown in FIG. 7.
Figure 22:
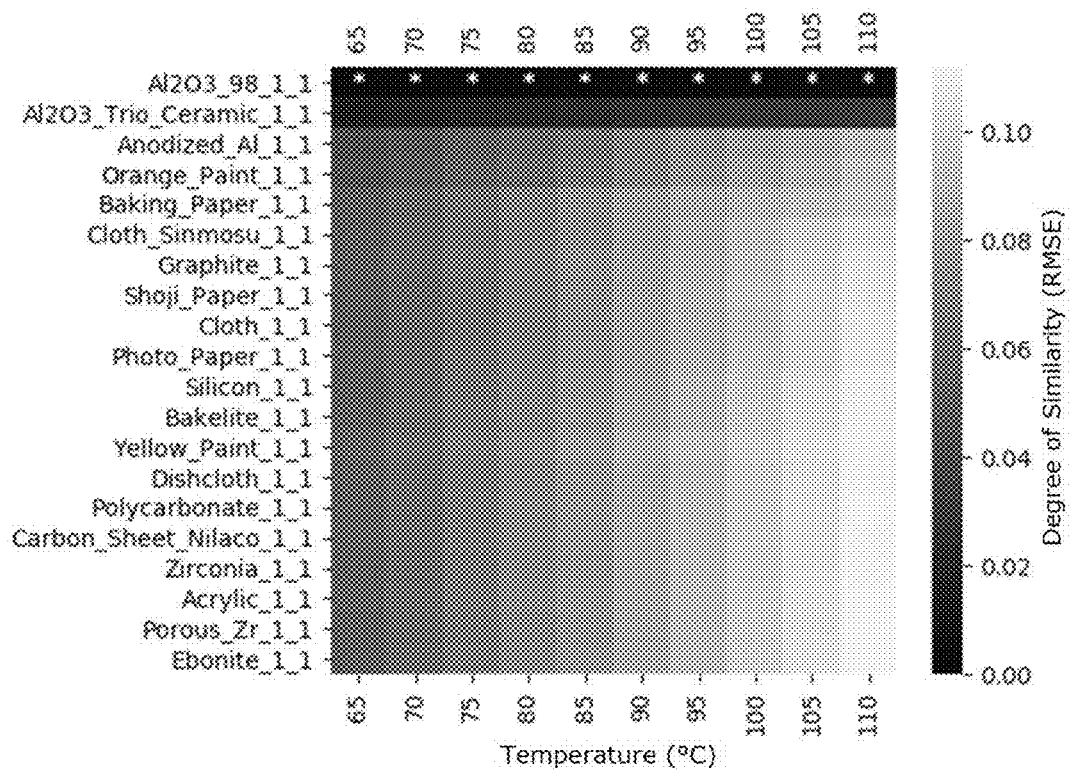
FIG. 22 shows the comparison and the identification results with the reference material in a case where alumina is used as the material of the target to be measured in one example of the present invention in the graphed diagram shown in FIG. 7.
Figure 23:
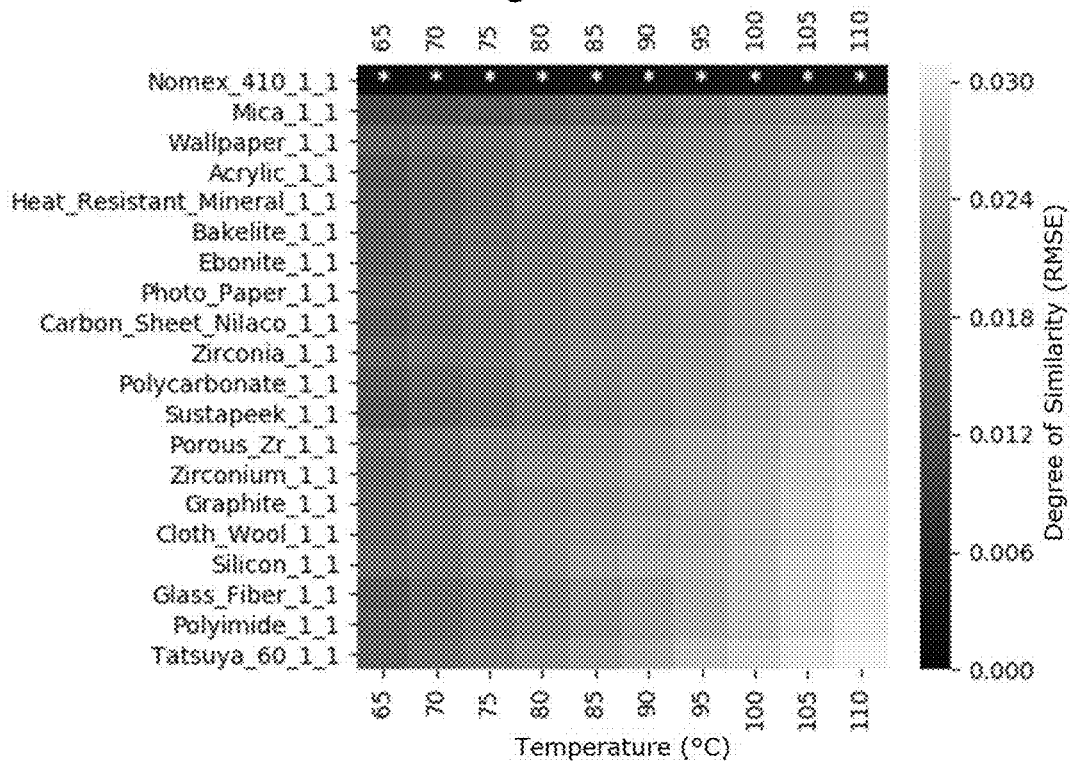
FIG. 23 shows the comparison and the identification results with the reference material in a case where Nomex (registered trademark) 410 sheet is used as the material of the target to be measured in one example of the present invention in the graphed diagram shown in FIG. 7.
Figure 24:
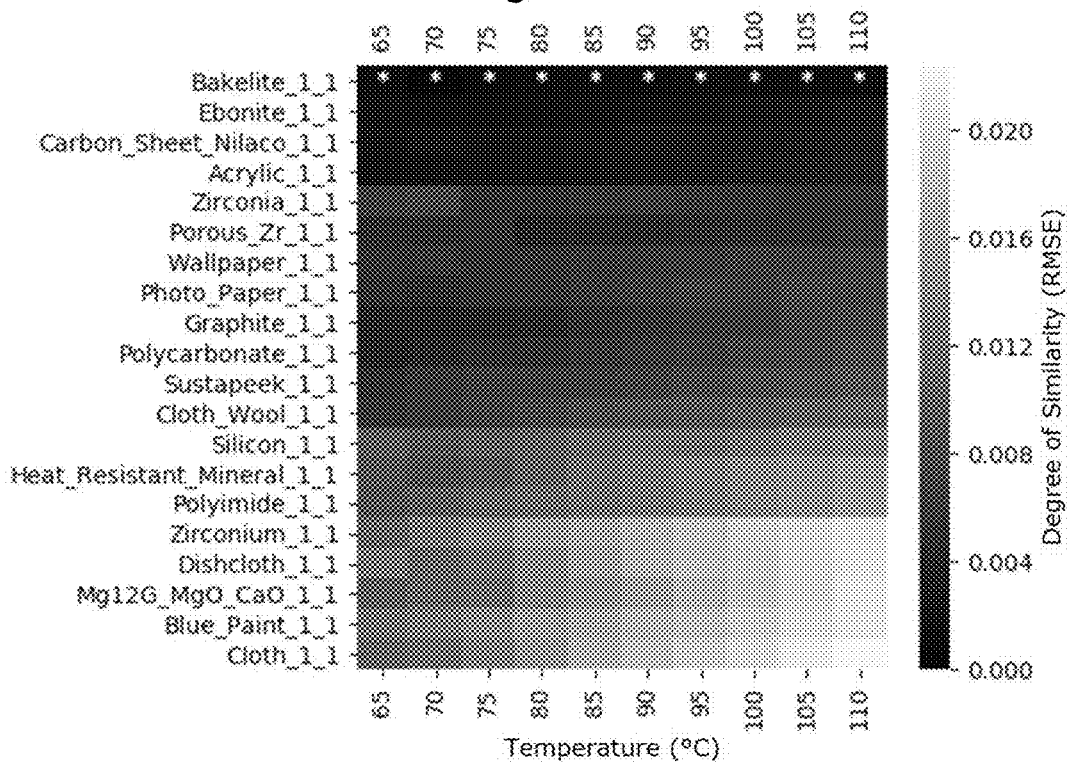
FIG. 24 shows the comparison and the identification results with the reference material in a case where Bakelite is used as the material of the target to be measured in one example of the present invention in the graphed diagram shown in FIG. 7.
Figure 25:
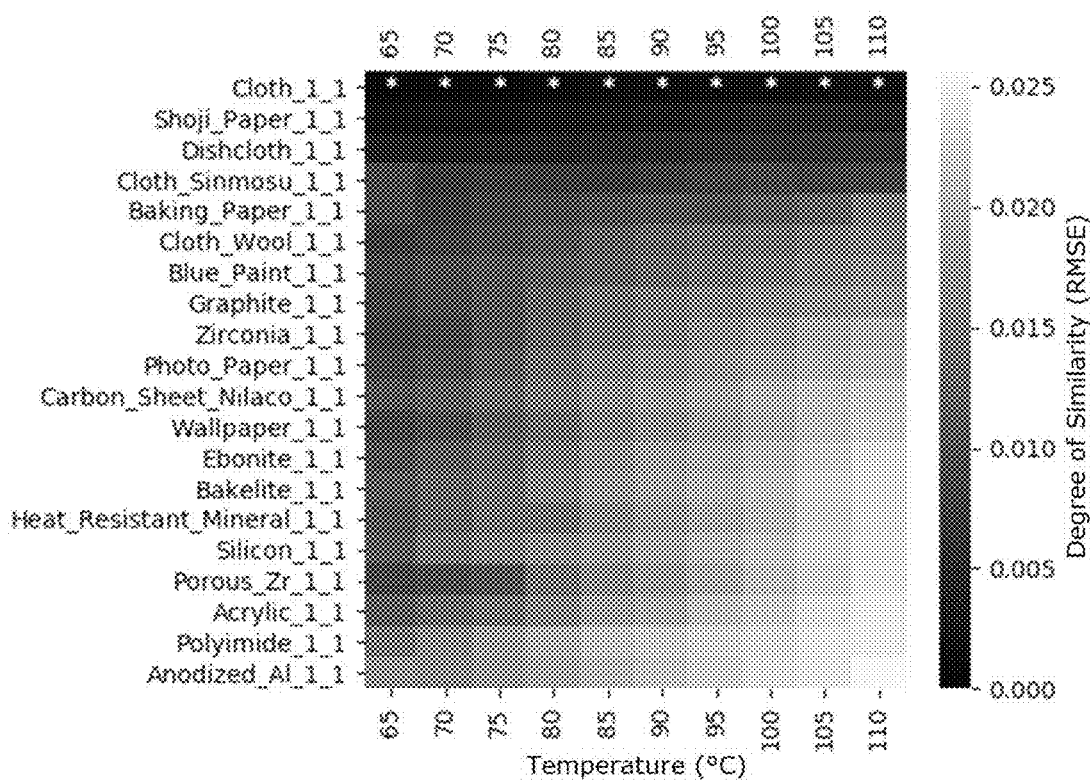
FIG. 25 shows the comparison and the identification results with the reference material in a case where a cloth is used as the material of the target to be measured in one example of the present invention in the graphed diagram shown in FIG. 7.

In addition, in a case where a part of erroneous identification has occurred (an erroneous identification between the tantalum and the aluminum shown in FIGS. 18 and 19), since both have considerably similar thermal radiation characteristics, instead of classifying materials from a viewpoint of a similarity of thermal radiation characteristics and identifying them as completely same, it is also possible to identify a class (in the examples above, the aluminum and the tantalum (or other metals can also belong thereto), plastics of a certain kind, and the like) to which the target to be measured belongs.

In the examples explained above, one piece of the reference data is prepared for one material. However, the plurality of pieces of data obtained by measuring the material under the same conditions can be prepared as the reference data corresponding to each material as described above. Here, the plurality of pieces of reference data corresponding to the same material often differ from one another due to the variations caused by measurement errors or the like. It is natural that, a case where they happen to be same is not excluded. The measurement results for identifying the material and/or the temperature, that is, the comparison with the data of the target to be measured can be performed. In the examples below, for some materials, the plurality of pieces of reference data obtained by the measurement performed for a plurality of times from the same material were prepared in the same measurement method as in a first example, and the reference data was compared with the data of the target to be measured obtained by measuring the target (however, the temperature was set every 5° C. in the range of 65° C. to 110° C. and measured) whose material is unknown in the same measurement method as in the first example in the same manner as in the first example. Examples of the material for which the reference data is obtained include an artificial mica (M), a flame-retardant meta-aramid fiber (N), the white paint (W), an inorganic mineral heat insulating sheet (H), a polyimide sheet (P), a silicon rubber sheet (S), and a porous zirconia (Z). Further, each piece of the reference data referred to herein is a set of data obtained by performing the measurement at different temperatures every 5° C. between 65° C. and 110° C. and repeating the measurement for a predetermined number of times (10 times in the present example). In the present example, such measurement is performed for eight times, and a numerical value up to 1 to 10 is added one character after the alphabet representing the material (for example, M-1, M-2, . . . , M10), thereby identifying the plurality of pieces of reference data for the material from one another. Naturally, data of 10 temperatures (every 5° C. in the range of 65° C. to 110° C.) was measured for each piece of reference data (for example, M-1) of each material to which each numerical value was assigned.

Figure 26:
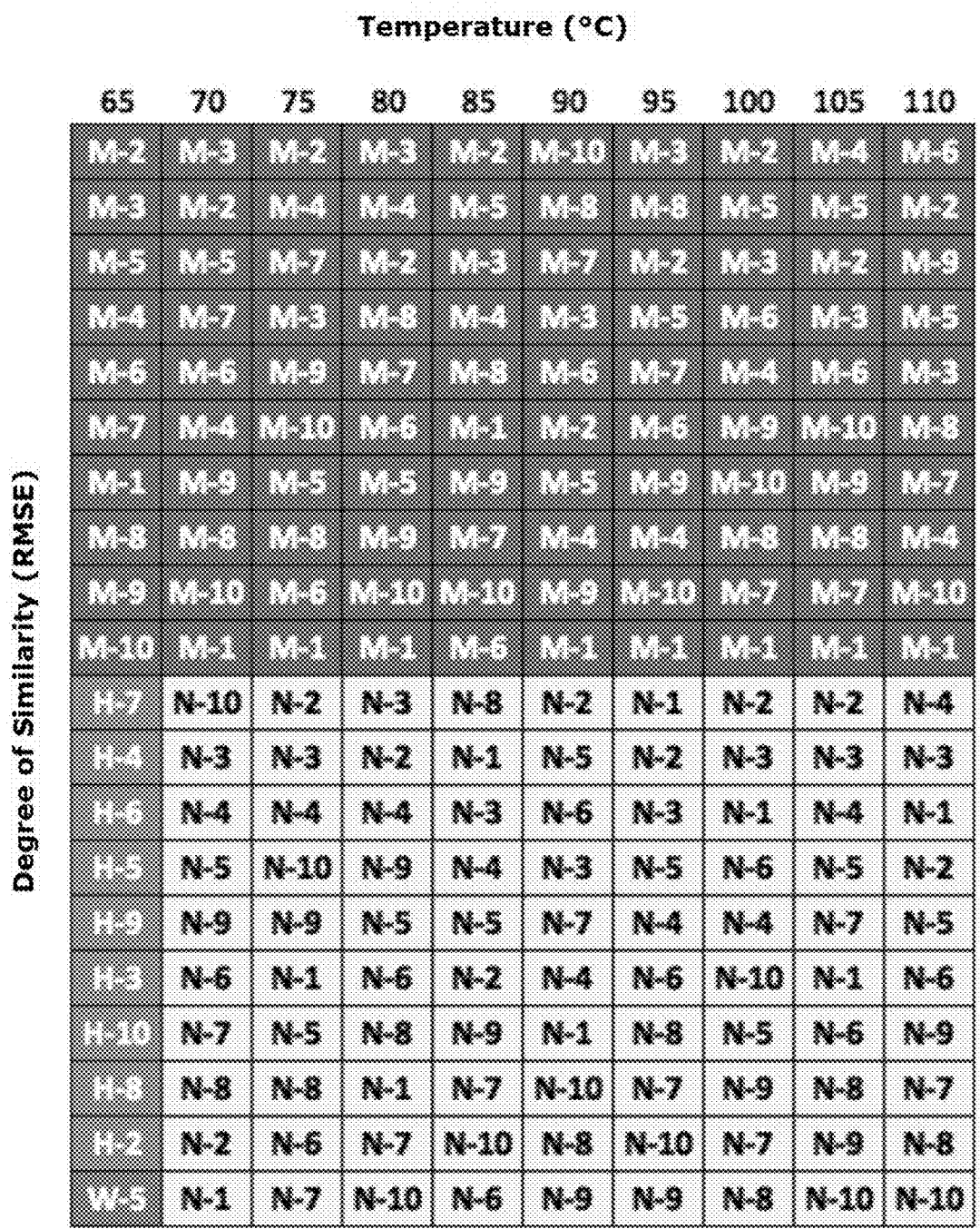
FIG. 26 shows a material discrimination result in a case where measurement is repeated in one example of the present invention, where artificial mica is an unknown sample. They are arranged in a descending order of degrees of similarity. The artificial mica ranked high, and an unknown material was determined to be artificial mica with high accuracy.

The artificial mica (M) and the polyimide sheet (P) were selected as materials of the target to be measured, and the measurement and the comparison above were performed. Results of arranging the reference data in a column direction from top to bottom in the ascending order of the root mean square error RMSE calculated by this comparison (that is, in the descending order of degrees of similarity) are shown in FIGS. 26 and 27, respectively. Further, in FIGS. 26 and 27, a row direction indicates the temperature in increments of 5° C. from 65° C. to 110° C. when the measurement is performed. As can be seen from the results shown in FIGS. 26 and 27, a top in a case where the root mean square errors RMSE are arranged in the ascending order is occupied by the reference data obtained from the same material in both the artificial mica and the polyimide sheet. In this measurement, the reference data from the same material occupied top 10 in any combination of the material and the temperature. When the same material is measured for a plurality of times (10 times in the present example) and the variation in the measured values of the reference data is large, these 10 pieces of reference data may not occupy the top of the root mean square errors. However, in such case, a probability that the comparison results with the reference data from the same material are ranked high is usually higher than that in the comparison results with the reference data from other materials. Accordingly, for example, the material of the target to be measured can be identified by taking the majority decision on the material corresponding to the reference data included in a higher order of the comparison results.

As described above, by using the thermal radiation, the material of the target to be measured can be identified with high accuracy by a direct and simple method of normalizing a reference data group and the data of the target to be measured obtained for the plurality of materials and then by obtaining the degrees of similarity between the reference data group and the data of the target to be measured when processing such as the machine learning is not particularly performed. Further, although not specifically mentioned in the examples above, it will also be apparent that both or one of the material and the temperature of the target to be measured can be identified by comparing the degrees of similarity between normalized reference data group and the data of the target to be measured by obtaining the reference data for the plurality of temperatures.

INDUSTRIAL APPLICABILITY

As described above, the present invention can identify the material and the temperature thereof by using the thermal radiation from the target, and thus can be used in a very wide field. Non-limiting examples include environment recognition sensors (road surface condition sensors, sensors of pedestrians, animals, and other things, and the like) that can be used for determination and sorting of various materials and objects, quality control of products during or after processing, and typically automatic driving of automobiles and the like. Further, it is also possible to improve performance of an infrared camera examination performed for a purpose of prevention of epidemics in application to security devices such as individual identification by measuring the thermal radiation from a human face or the like, and entrance control. Furthermore, since the target can be in a gas phase, the present invention can also be applied to, for example, a gas sensor such as a humidity sensor or a carbon dioxide sensor, a test of exhaust gas from an automobile engine or other various combustion engines, and detection of poisonous gas. Further, it is also effective as a method for analyzing and monitoring deterioration over time of foods; product parts; and buildings; or deterioration of materials and objects, and changes in materials that are desired to avoid damage and deterioration as much as possible, such as works of art and museum exhibits in a non-contact, non-destructive, and non-damage manner without irradiating observation X-rays, electron beams, and ultraviolet rays. Furthermore, it is also effective as a method of monitoring a change in an environment such as a change in distribution of a component gas or a temperature thereof by measuring radiation from a gas in an office or the like.

CITATION LIST

Patent Literature

Patent Literature 1: U.S. Pat. No. 4,561,786

Non Patent Literature

Non Patent Literature 1: NDE Handbook: Non-Destructive Examination Methods for Condition Monitoring, Knud G. Boving Eds. (1987), By Elsevier Science.

Non Patent Literature 2: T. D. Dao et al, Adv. Sci. 6, 1900579(2019).

Non Patent Literature 3: https://spectrabase.com/.

Non Patent Literature 4: Antonio Araujo, Multi-spectral pyrometry—a review, Meas. Sci. Technol. 28, 082002 (2017).

Non Patent Literature 5: Jiafeng Liang et al., Generalized inverse matrix-exterior penalty function (GIM-EPF) algorithm for data processing of multi-wavelength pyrometer (MWP), OPTICS EXPRESS, Vol. 26, No. 20 25706-25720 (2018).

The invention claimed is:

1. A method for identifying a material in a non-contact manner by measuring a target to be measured as a thermal radiation light source comprising:
  comparing degrees of similarity between intensity data and at least one of reference data and combined reference data, the intensity data being a combination of thermal radiation intensities at three wavelengths or more wavelengths in an infrared band radiated from the target to be measured itself, the reference data being a combination of thermal radiation intensity data at a plurality of wavelengths in the infrared band from each of a plurality of different candidate materials for identifying a material of the target to be measured, and the combined reference data being of a mixture of the plurality of different materials obtained by combining a plurality of pieces of the reference data based on the plurality of different materials; and identifying the material of the target as the candidate material or a mixture thereof corresponding to one or more pieces of the reference data or the combined reference data having the highest degree of similarity.

2. The method for identifying the material in the non-contact manner according to claim 1, wherein the comparison of the degrees of similarity is performed for at least all pieces of the combined reference data.

3. The method for identifying the material in the non-contact manner according to claim 1, wherein a solving method for a combinatorial optimization problem is applied to the comparison of the degrees of similarity and the identification.

4. The method for identifying the material in the non-contact manner according to claim 1, wherein, processing is performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

5. The method for identifying the material in the non-contact manner according to claim 1, wherein the target to be measured is a solid, a liquid, a gas, or a mixture thereof.

6. The method for identifying the material in the non-contact manner according to claim 1, wherein the reference data is intensity data measured at a plurality of discrete wavelengths.

7. The method for identifying the material in the non-contact manner according to claim 6, wherein the plurality of wavelengths is at least three wavelengths.

8. The method for identifying the material in the non-contact manner according to claim 1, wherein the degrees of similarity are determined based on a difference in intensities between the intensity data and the reference data at the plurality of wavelengths.

9. The method for identifying the material in the non-contact manner according to claim 1, wherein the reference data is a combination of a plurality of temperatures that are candidates for material identification of the target to be measured and the thermal radiation intensity data at the plurality of wavelengths in the infrared band for each of the plurality of different materials.

10. The method for identifying the material in the non-contact manner according to claim 9, wherein the degrees of similarity are determined based on a difference in intensities between the intensity data and the reference data at the plurality of wavelengths for each temperature.

11. The method for identifying the material in the non-contact manner according to claim 9, wherein the temperature of the target to be measured is further identified based on the comparison of the degree of similarity, and at least one of the identified material and temperature of the target to be measured is presented as an identification result.

12. The method for identifying the material in the non-contact manner according to claim 1, wherein the degrees of similarity are obtained after normalizing each piece of the intensity data and the reference data.

13. The method for identifying the material in the non-contact manner according to claim 1, wherein the thermal radiation from an object other than the target to be measured is removed using an optical system.

14. The method for identifying the material in the non-contact manner according to claim 1, wherein the degrees of similarity are determined based on a root mean square error between the intensity data and the reference data.

15. A method for identifying a product during processing, or a state of the processing, a progress of the processing, or normality of the processing in a heat treatment process comprising:

comparing degrees of similarity between intensity data and at least one of reference data and combined reference data for each predetermined step of processing in a heat treatment process of a material, the intensity data being a combination of thermal radiation intensities at a plurality of wavelengths in an infrared band radiated from the material itself, the reference data being a combination of the thermal radiation intensities at the plurality of wavelengths in the infrared band radiated from the same kind of the material itself obtained at predetermined steps of processing in a heat treatment process of a plurality of different materials of the same kind as the material, and the combined reference data being of a mixture of the plurality of different materials obtained by combining the plurality of pieces of the reference data based on the plurality of different materials; and identifying one or more pieces of the reference data or the combined reference data having the highest degree of similarity.

16. The method for identifying the product during processing, or the state of the processing, the progress of the processing, or the normality of the processing in the heat treatment process according to claim 15, wherein, processing is performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

17. The method for identifying the product during processing, or the state of the processing, the progress of the processing, or the normality of the processing in the heat treatment process according to claim 15, wherein the reference data further includes a combination of the thermal radiation intensities at the plurality of wavelengths in an infrared band radiated from a defective material itself that can be generated by abnormal progress in the heat treatment process of the material.

18. A method for detecting a material change that is a change of a material being a target to be measured from a reference material by:

comparing degrees of similarity between intensity data and at least one of reference data and combined reference data, the intensity data being a combination of thermal radiation intensities at a plurality of wavelengths in an infrared band radiated from the material of the target to be measured itself, the reference data being a combination of the thermal radiation intensities at the plurality of wavelengths in the infrared band radiated from the reference material itself that is a plurality of different materials of the same kind as the material of the target to be measured, and the combined reference data being of a mixture of the plurality of different materials obtained by combining the plurality pieces of reference data based on the plurality of different materials, and identifying one or more pieces of the reference data or the combined reference data having the highest degree of similarity.

19. The method for detecting the material change according to claim 18, wherein, processing is performed in obtaining the degrees of similarity, the processing being selected from a group consisting of extracting points or feature values to be used for obtaining the degrees of similarity from at least one of the reference data and the combined reference data, and dividing at least one of the reference data and the combined reference data into a plurality of classes and subjecting a part of the plurality of classes to the comparison of the degrees of similarity.

20. The method for detecting the material change according to claim 18, wherein the reference data further includes the intensity data upon the reference material changing to an abnormal state.

* * * * *